(12) United States Patent
Sharkey et al.

(10) Patent No.: US 7,303,526 B2
(45) Date of Patent: ***Dec. 4, 2007

(54) DEVICE FOR IMPROVING CARDIAC FUNCTION

(75) Inventors: Hugh R. Sharkey, Redwood City, CA (US); Serjan D. Nikolic, San Francisco, CA (US); Branislav Radovancevic, Houston, TX (US)

(73) Assignee: Cardiokinetix, Inc., Redwood City, CA (US)

( * ) Notice: Subject to any disclaimer, the term of this patent is extended or adjusted under 35 U.S.C. 154(b) by 386 days.

This patent is subject to a terminal disclaimer.

(21) Appl. No.: 10/212,033

(22) Filed: Aug. 1, 2002

(65) Prior Publication Data

US 2003/0050682 A1 Mar. 13, 2003

Related U.S. Application Data

(63) Continuation-in-part of application No. 09/635,511, filed on Aug. 9, 2000, now abandoned.

(60) Provisional application No. 60/147,894, filed on Aug. 9, 1999.

(51) Int. Cl.
*A61F 2/00* (2006.01)
(52) U.S. Cl. ........................................ 600/37; 623/910
(58) Field of Classification Search ................ 600/375, 600/16, 37; 606/213; 607/126, 128; 623/3.1, 623/11.1, 904, 910, 913, 922; 604/508
See application file for complete search history.

(56) References Cited

U.S. PATENT DOCUMENTS 3,874,388 A    4/1975   King et al.
4,007,743 A    2/1977   Blake
4,425,908 A    1/1984   Simon
4,619,246 A    10/1986  Molgaard-Nielsen et al.
4,710,192 A    12/1987  Liotta et al.
4,832,055 A    5/1989   Palestrant
4,917,089 A *  4/1990   Sideris .................. 606/215
5,104,399 A    4/1992   Lazarus (Continued)

FOREIGN PATENT DOCUMENTS

WO    WO 00/27292    5/2000

(Continued)

OTHER PUBLICATIONS

Kawata, et al., "Systolic and Diastolic Function After Patch Reconstruction of Left Ventricular Aneurysms," Ann. Thorac. Surg. 59, pp. 403-407, 1995.

(Continued)

*Primary Examiner*—Scott Getzow
(74) *Attorney, Agent, or Firm*—Shay Law Group LLP

(57) ABSTRACT

A method and a device for improving cardiac function are provided. The device is packaged in a collapsed state in an end of a catheter. Portions of a frame construction of the device spring outwardly when the catheter is withdrawn from the device. Anchoring formations on the frame construction secure the frame construction to a myocardium of the heart. A membrane secured to the frame construction then forms a division between volumes of an endocardial cavity of the heart on opposing sides of the membrane.

47 Claims, 20 Drawing Sheets

U.S. PATENT DOCUMENTS

| | | | |
|---|---|---|---|
| 5,192,301 A * | 3/1993 | Kamiya et al. | 606/213 |
| 5,192,314 A | 3/1993 | Daskalakis et al. | |
| 5,375,612 A | 12/1994 | Cottenceau et al. | |
| 5,385,156 A | 1/1995 | Oliva | |
| 5,425,744 A * | 6/1995 | Fagan et al. | 606/213 |
| 5,433,727 A * | 7/1995 | Sideris | 606/213 |
| 5,451,235 A * | 9/1995 | Lock et al. | 606/213 |
| 5,496,277 A | 3/1996 | Termin et al. | |
| 5,527,337 A | 6/1996 | Stack et al. | |
| 5,527,338 A | 6/1996 | Purdy | |
| 5,549,621 A | 8/1996 | Bessler et al. | |
| 5,578,069 A * | 11/1996 | Miner, II | 607/126 |
| 5,634,936 A | 6/1997 | Linden et al. | |
| 5,634,942 A | 6/1997 | Chevillon et al. | |
| 5,702,343 A | 12/1997 | Alferness | |
| 5,709,707 A * | 1/1998 | Lock et al. | 606/213 |
| 5,791,231 A | 8/1998 | Cohn et al. | |
| 5,797,849 A | 8/1998 | Vesely et al. | |
| 5,797,960 A | 8/1998 | Stevens et al. | |
| 5,829,447 A | 11/1998 | Stevens et al. | |
| 5,833,698 A | 11/1998 | Hinchliffe et al. | |
| 5,836,968 A | 11/1998 | Simon et al. | |
| 5,843,170 A | 12/1998 | Ahn | |
| 5,861,003 A | 1/1999 | Latson et al. | |
| 5,865,730 A | 2/1999 | Fox et al. | |
| 5,865,791 A | 2/1999 | Whayne et al. | |
| 5,871,017 A | 2/1999 | Mayer | |
| 5,875,782 A | 3/1999 | Ferrari et al. | |
| 5,876,325 A | 3/1999 | Mizuno et al. | |
| 5,876,449 A | 3/1999 | Starck et al. | |
| 5,879,366 A | 3/1999 | Shaw et al. | |
| 5,882,340 A | 3/1999 | Yoon | |
| 5,910,150 A | 6/1999 | Saadat | |
| 5,916,145 A | 6/1999 | Chu et al. | |
| 5,924,424 A | 7/1999 | Stevens et al. | |
| 5,925,076 A | 7/1999 | Inoue | |
| 5,928,260 A | 7/1999 | Chin et al. | |
| 5,961,440 A | 10/1999 | Schweich, Jr. et al. | |
| 5,961,539 A | 10/1999 | Northrup, III et al. | |
| 5,984,917 A | 11/1999 | Fleischman et al. | |
| 6,024,096 A | 2/2000 | Buckberg | |
| 6,024,756 A | 2/2000 | Huebsch et al. | |
| 6,045,497 A | 4/2000 | Schweich et al. | |
| 6,059,715 A | 5/2000 | Schweich et al. | |
| 6,076,013 A | 6/2000 | Brennan et al. | |
| 6,077,214 A | 6/2000 | Mortier et al. | |
| 6,077,218 A | 6/2000 | Alferness | |
| 6,093,199 A | 7/2000 | Brown et al. | |
| 6,095,968 A | 8/2000 | Snyders | |
| 6,096,347 A | 8/2000 | Geddes et al. | |
| 6,099,832 A | 8/2000 | Mickle et al. | |
| 6,102,887 A | 8/2000 | Altman | |
| 6,125,852 A | 10/2000 | Stevens et al. | |
| 6,132,438 A | 10/2000 | Fleischman et al. | |
| 6,152,144 A | 11/2000 | Lesh et al. | |
| 6,161,543 A | 12/2000 | Cox et al. | |
| 6,193,731 B1 | 2/2001 | Oppelt et al. | |
| 6,221,092 B1 | 4/2001 | Koike et al. | |
| 6,231,561 B1 | 5/2001 | Frazier et al. | |
| 6,258,021 B1 | 7/2001 | Wilk | |
| 6,267,772 B1 | 7/2001 | Mulhauser et al. | |
| 6,290,674 B1 | 9/2001 | Roue et al. | |
| 6,312,446 B1 | 11/2001 | Huebsch et al. | |
| 6,328,727 B1 | 12/2001 | Frazier et al. | |
| 6,334,864 B1 | 1/2002 | Amplatz et al. | |
| 6,343,605 B1 | 2/2002 | Lafontaine | |
| 6,348,068 B1 | 2/2002 | Campbell et al. | |
| 6,355,052 B1 | 3/2002 | Neuss et al. | |
| 6,360,749 B1 | 3/2002 | Jayaraman | |
| 6,364,896 B1 | 4/2002 | Addis | |
| 6,387,042 B1 | 5/2002 | Herrero | |
| 6,406,420 B1 * | 6/2002 | McCarthy et al. | 600/16 |
| 6,419,669 B1 | 7/2002 | Frazier et al. | |
| 6,436,088 B2 | 8/2002 | Frazier et al. | |
| 6,450,171 B1 | 9/2002 | Buckberg | |
| 6,482,228 B1 | 11/2002 | Norred | |
| 6,506,204 B2 | 1/2003 | Mazzocchi | |
| 6,537,198 B1 | 3/2003 | Vidlund et al. | |
| 6,551,303 B1 | 4/2003 | Van Tassel et al. | |
| 6,592,608 B2 | 7/2003 | Fisher et al. | |
| 6,652,555 B1 * | 11/2003 | VanTassel et al. | 606/200 |
| 6,685,627 B2 | 2/2004 | Jayaraman | |
| 6,852,076 B2 * | 2/2005 | Nikolic et al. | 600/37 |
| 2001/0014800 A1 | 8/2001 | Frazier et al. | |
| 2002/0019580 A1 | 2/2002 | Lau et al. | |
| 2002/0026092 A1 * | 2/2002 | Buckberg et al. | 600/37 |
| 2002/0028981 A1 | 3/2002 | Lau et al. | |
| 2002/0032481 A1 | 3/2002 | Gabbay | |
| 2002/0055767 A1 | 5/2002 | Forde et al. | |
| 2002/0055775 A1 | 5/2002 | Carpentier et al. | |
| 2002/0161394 A1 | 10/2002 | Macoviak et al. | |
| 2002/0169359 A1 | 11/2002 | McCarthy et al. | |
| 2002/0169360 A1 | 11/2002 | Taylor et al. | |
| 2002/0188170 A1 | 12/2002 | Santamore et al. | |
| 2003/0050685 A1 | 3/2003 | Nikolic et al. | |
| 2003/0105384 A1 | 6/2003 | Sharkey et al. | |
| 2003/0109770 A1 | 6/2003 | Sharkey et al. | |
| 2003/0120337 A1 | 6/2003 | Van Tassel et al. | |
| 2003/0149333 A1 | 8/2003 | Alferness | |
| 2003/0220667 A1 | 11/2003 | Van Der Burg et al. | |
| 2004/0002626 A1 | 1/2004 | Feld et al. | |
| 2005/0154252 A1 | 7/2005 | Sharkey et al. | |
| 2005/0197716 A1 | 9/2005 | Sharkey et al. | |
| 2005/0216052 A1 | 9/2005 | Mazzocchi et al. | |
| 2006/0014998 A1 | 1/2006 | Sharkey et al. | |
| 2006/0030881 A1 | 2/2006 | Sharkey et al. | |

FOREIGN PATENT DOCUMENTS

| | | |
|---|---|---|
| WO | WO 01/30266 | 5/2001 |
| WO | WO 01/78625 A1 | 10/2001 |
| WO | WO 02/30335 | 4/2002 |
| WO | WO 02/071977 A2 | 9/2002 |
| WO | WO 03/007778 A | 1/2003 |
| WO | WO 2004/012629 A | 2/2004 |
| WO | WO 2004/100803 | 11/2004 |
| WO | WO 2005/007031 | 1/2005 |

OTHER PUBLICATIONS

Dor, "The Treatment of Refractory Ischemic Ventricular Tachycardia . . . ," Seminars in Thoracic and Cardiovascular Surgery, vol. 9, No. 2, pp. 146-155, Apr. 1997.

Di Mattia, et al., "Surgical treatment of left ventricular post-infarction aneurysm . . . ," European Journal of Cardio-thoracic Surgery 15, pp. 413-419, 1999.

Katsumata, et al., "An objective appraisal of partial left ventriculectomy . . . ," Journal of Congestive Heart Failure and Circulator Support, pp. 97-106, 1999.

Dor, "Surgery for left ventricular aneurysm," Current Opinion in Cardiology, Current Science, pp. 773-780, 1990.

Dor, et al., "Ventricular remodeling in coronary artery disease," Current Opinion in Cardiology, Rapid Science Publishers, pp. 533-537, 1997.

AGA Medical Corporation, www.amplatzer.com/products, "The Muscular VSD Occluder" and "The Septal Occluder" device descriptions, Apr. 3, 2002.

Gore Medical, www.goremedical.com, "Helex Septal Occluder" product description, Apr. 3, 2002.

Tetsuji Kawata et al., "Systolic and Diastolic Function After Patch Reconstruction of Left Ventricular Aneurysms", Ann. Thorac. Surg. 59, pp. 403-407, 1995.

Vincent Dor, "The Treatment of Refractory Ischemic Ventricular Tachycardia by Endoventricilar Patch Plasty Reconstruction of the Left Ventricle", Seminars in Thoracic and Cardiovascular Surgery, vol. 9, No. 2, pp. 146-155, Apr. 1997.

Daniel Giorgio Di Mattia, et al., "Surgical treatment of left ventricular post-infarction aneurysm with endoventriculoplasty: late clinical and functional results", European Journal of Cardio-thoracic Surgery 15, pp. 413-419, 1999.

T. Katsumata, et al., "An objective appraisal of partial left ventriculectomy for heart failure", Journal of Congestive Heart Failure and Circulator Support, pp. 97-106, 1999.

Vincent Dor, "Surgery for left ventricular aneurysm", Current Opinion in Cardiology, Current Science, pp. 773-780, 1990.

Vincent Dor et al., "Ventricular remodeling in coronary artery disease", Current Opinion in Cardiology, Rapid Science Publishers, pp. 533-537, 1997.

International Search Report and Written Opinion for PCT/US2004/014782 mailed Sep. 21, 2004.

International Search Report and Written Opinion for PCT/US2005/000264 mailed Apr. 26, 2005.

Khairkhahan, et al., U.S. Appl. No. 10/436,959, entitled "System for improving cardiac function," filed May 12, 2003.

Khairkhahan, et al., U.S. Appl. No. 11/151,164, entitled "Peripheral seal for a ventricular partitioning device," filed Jun. 10, 2005.

Sharkey, et al., U.S. Appl. No. 11/199,633, entitled "Method for treating myocardial rupture," filed Aug. 9, 2005.

* cited by examiner

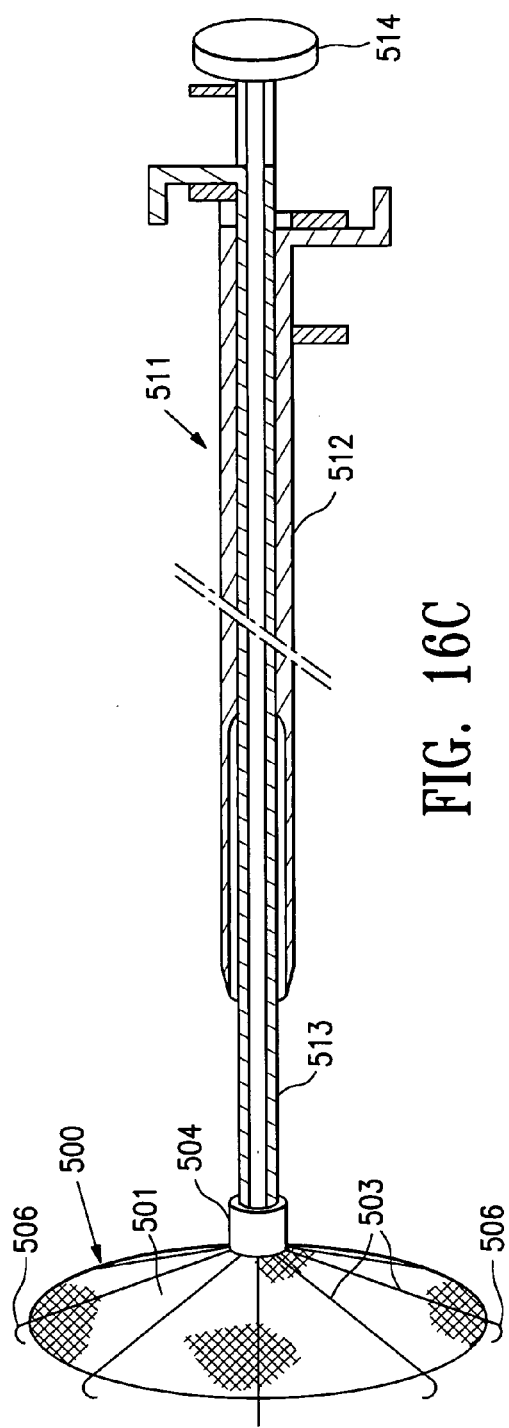
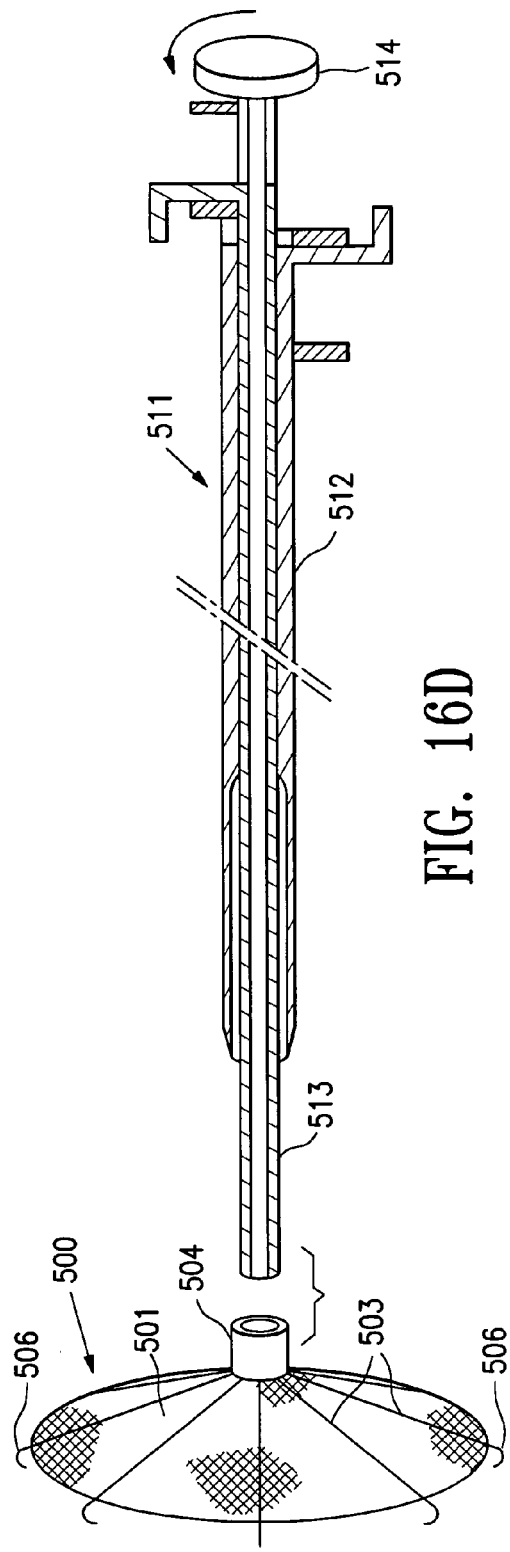
FIG. 16C
FIG. 16D

DEVICE FOR IMPROVING CARDIAC FUNCTION

CROSS-REFERENCE TO RELATED APPLICATIONS

The present patent application is a continuation-in-part application of prior U.S. patent application Ser. No. 09/635,511, filed on Aug. 9, 2000 now abandoned, which claims priority from U.S. Provisional Patent Application No. 60/147,894 filed on Aug. 9, 1999, and are incorporated herein by reference in their entirety.

BACKGROUND OF THE INVENTION

1). Field of the Invention

This invention relates to a method and device for improving cardiac function.

2). Discussion of Related Art

Congestive heart failure annually leads to millions of hospital visits internationally. Congestive heart failure is a description given to a myriad of symptoms that can be the result of the heart's inability to meet the body's demand for blood flow. In certain pathological conditions, the ventricles of the heart become ineffective in pumping the blood, causing a back-up of pressure in the vascular system behind the ventricle.

The reduced effectiveness of the heart is usually due to an enlargement of the heart. A myocardial ischaemia may, for example, cause a portion of a myocardium of the heart to lose its ability to contract. Prolonged ischemia can lead to infarction of a portion of the myocardium (heart muscle) wherein the heart muscle dies and becomes scar tissue. Once this tissue dies it no longer functions as a muscle and cannot contribute to the pumping action of the heart. When the heart tissue is no longer pumping effectively, that portion of the myocardium is said to be hypokinetic, meaning that it is less contractile than the uncompromised myocardial tissue. As this situation worsens, the local area of compromised myocardium may in fact bulge out as the heart contracts, further decreasing the heart's ability to move blood forward. When local wall motion moves in this way it is said to be dyskinetic. The dyskinetic portion of the myocardium may stretch and eventually form an aneurysmic bulge. Certain diseases may cause a global dilated myopathy, i.e., a general enlargement of the heart when this situation continues for an extended period of time. As the heart begins to fail, the filling pressures increase, which stretches the ventricular chamber prior to contraction, greatly increasing the pressure (preload) to the heart. In response, the heart tissue remodels to accommodate the chronically increased filling pressures, further increasing the work that the now-compromised myocardium must perform. This vicious cycle of cardiac failure results in the symptoms of congestive heart failure such as shortness of breath on exertion, edema in the periphery, nocturnal dypsnia (a characteristic shortness of breath that occurs at night after going to bed), weight gain, and fatigue, to name a few. The enlargements increase stress on the myocardium. The stress increase requires a larger amount of oxygen supply, which can result in exhaustion of the myocardium leading to a reduced cardiac output of the heart.

SUMMARY OF THE INVENTION

This invention relates to a device for improving cardiac function. The device has a frame construction that is movable from a collapsed state, wherein the frame construction has a small cross-dimension to allow the frame construction to be fed through a tubular passage with a small diameter into the heart, to an expanded state wherein the frame construction, after leaving the tubular passage and having been located in an installed position in an endocardial cavity of the heart, has a cross-dimension substantially larger than the small diameter of the tubular passage and approximating a cross-dimension of the endocardial cavity where the frame construction is positioned. The device has at least one anchor formation connected to the frame construction, having at least one anchoring portion that is positioned and capable of anchoring to tissue of a myocardium of the heart, and so anchor the frame construction in the installed position to the myocardium. The device further has a membrane which is in a folded condition when being fed through the tubular passage, and in an unfolded condition after leaving the tubular passage, in the unfolded condition having an area substantially larger than a cross-sectional area of the tubular passage, and being secured to the frame construction in a position to substantially form a division between volumes of the endocardial cavity on opposing sides of the membrane.

According to one aspect of the invention, at least two anchoring formations are connected to the frame construction, and are spaced from one another to allow for positioning of the frame construction at a select angle relative to the endocardial cavity.

According to another aspect of the invention, the frame construction is deformable into various non-circular shapes to allow for positioning thereof in endocardial cavities having differing non-circular shapes.

According to a further aspect of the invention, the frame construction includes a support frame next to and supporting the membrane, the support frame being sufficiently strong to support the membrane when a ventricular pressure acts on the membrane.

BRIEF DESCRIPTION OF THE DRAWINGS

The invention is further described by way of examples with reference to the accompanying drawings, wherein.

DETAILED DESCRIPTION OF THE INVENTION

Figure 1A:
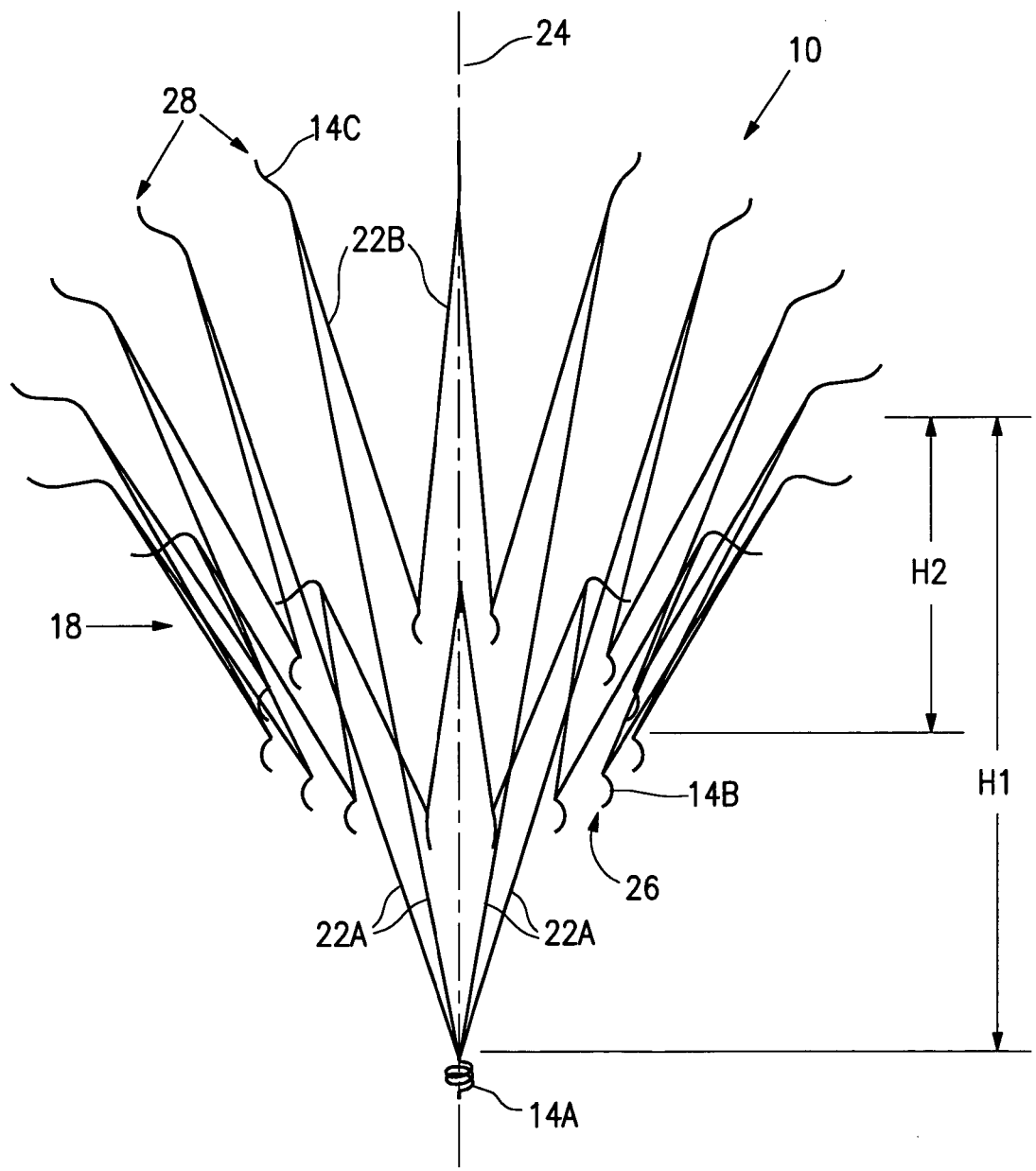
FIG. 1A is a perspective view of a main frame of a device, according to an embodiment of the invention, for improving cardiac function.
Figure 1B:
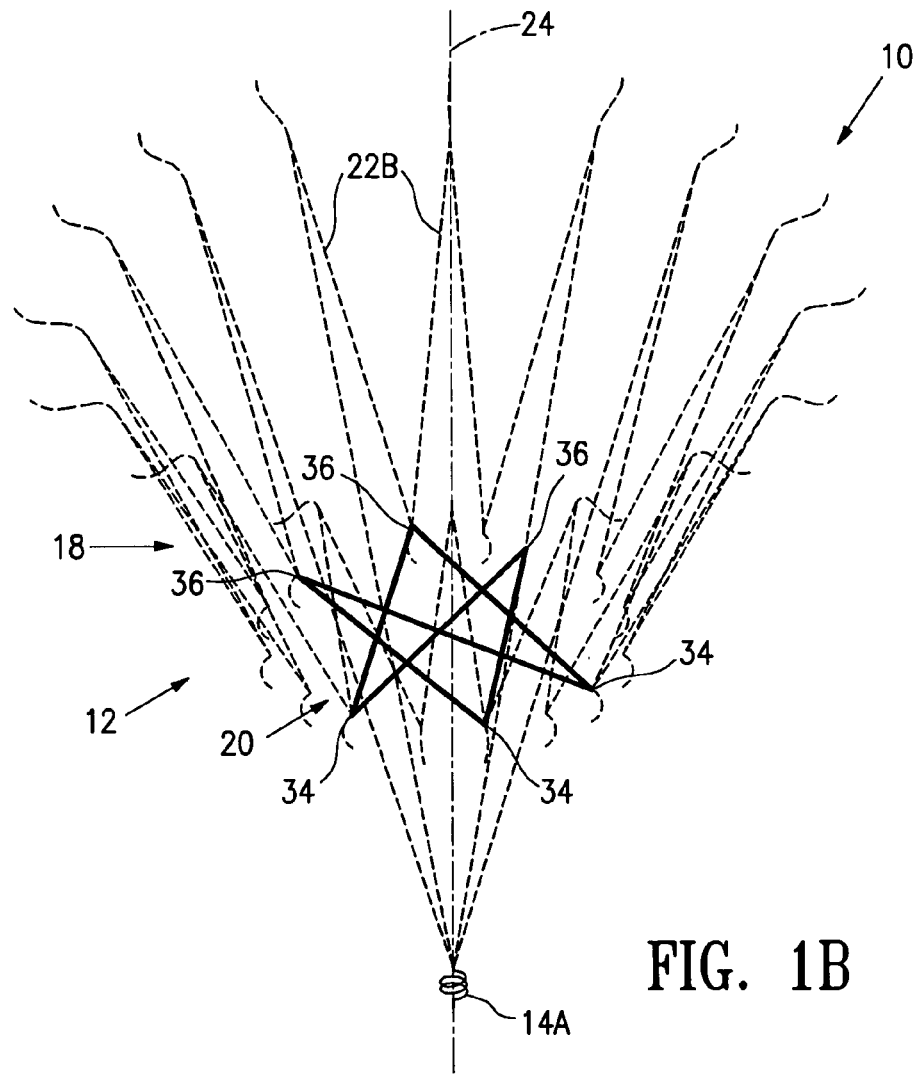
FIG. 1B is a view similar to FIG. 1A, illustrating the main frame in hidden lines and further illustrating in solid lines a support frame of the device mounted to the main frame.
Figure 1C:
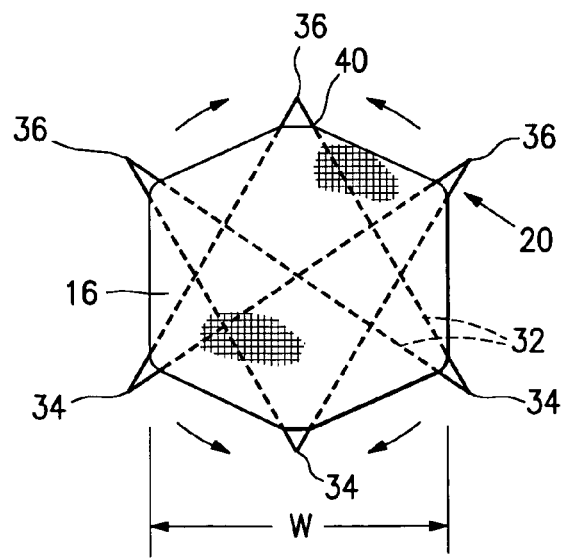
FIG. 1C is a top plan view illustrating a membrane of the device secured on top of the support frame.

FIGS. 1A, 1B, and 1C illustrate components of a device 10, according to an embodiment of the invention, for improving cardiac function. The device 10 includes a frame construction 12, a plurality of anchoring formations 14, and a membrane 16. The frame construction 12 includes a main frame 18 and a support frame 20 secured to the main frame 18. The membrane 16 is secured on top of the support frame 20.

As shown in FIG. 1A, the main frame 18 includes a sequence or series of segments 22. Even segments of the series extend in an upward direction, and odd segments extend downward. The sequence formed by the segments 22 entirely surrounds a vertical axis 24. Movement of the segments 22 toward one another causes collapse of the main frame 18 toward the vertical axis 24. The frame construction 12 is made of a biocompatible wire-like shape-memory material, for example, nickel-titanium.

The anchoring formations 14 include a distal anchoring screw 14A, distal anchoring hooks 14B, and proximal anchoring hooks 14C. Two or more (in the present example, four) of the segments 22A are longer, and extend further down than other ones of the segments 22B. The segments 22A have their lower ends connected to one another, and the distal anchoring screw 14A is secured to the lower ends of the segments 22A. The segments 22A and 22B may be curved, as opposed to being straight as shown in the figures.

The distal anchoring hooks 14B are secured to lower ends of the segments 22B. Each distal anchoring hook 14B curves out and then down and is formed with a lower sharp end 26.

The proximal anchoring hooks 14C are secured to upper ends of the segments 22A and 22B. Each one of the proximal anchoring hooks 14C curves out and then up and terminates in an upper sharp end 28. The anchoring hooks 14B and 14C move together with the main frame 18 toward the vertical axis 24 when the main frame 18 is collapsed.

As shown in FIG. 1C, the support frame 20 includes six (or more) elements 32, sequentially after one another and overlaying one another to form a six-pointed star. The elements 32 can pivot in a scissor-like manner relative to one another. Pivoting of the elements 32 relative to one another moves corners 34 of the star toward one another, while corners 36 on an opposing side of the star move toward one another. The support frame 20 then has an elongated configuration with the corners 36 at one end and the corners 34 at an opposing end.

Referring to FIG. 1B, each corner 36 is positioned around and slidably secured to a respective one of the segments 22B. When the main frame 18 is collapsed, the corners 34 slide up the segments 22B to which they are secured, while the corners 36 remain at the bottom of the segments 22B to which they are secured. When the main frame 18 is fully collapsed, the support frame 20 is in the form of an elongated arrangement extending along the vertical axis 24, with the corners 34 at the top and the corners 36 at the bottom.

FIG. 1C also shows the membrane 16, in an unfolded condition, secured on the elements 32 of the support frame 20. An edge 40 of the membrane 16 is secured to the elements 32. Two of the elements 32 form a cross below a center of the membrane 16, and the other four elements 32 support the membrane 16 between the cross and the edge 40. Collapse of the support frame 20 folds the membrane 16 into an elongated folded arrangement extending along the elongated arrangement formed by the collapsed support frame 20. The membrane 16 is made of a biocompatible foldable material, for example Gore-Tex®, poly-ethylene terephthalate, or polypropylene mesh.

Figure 2A:
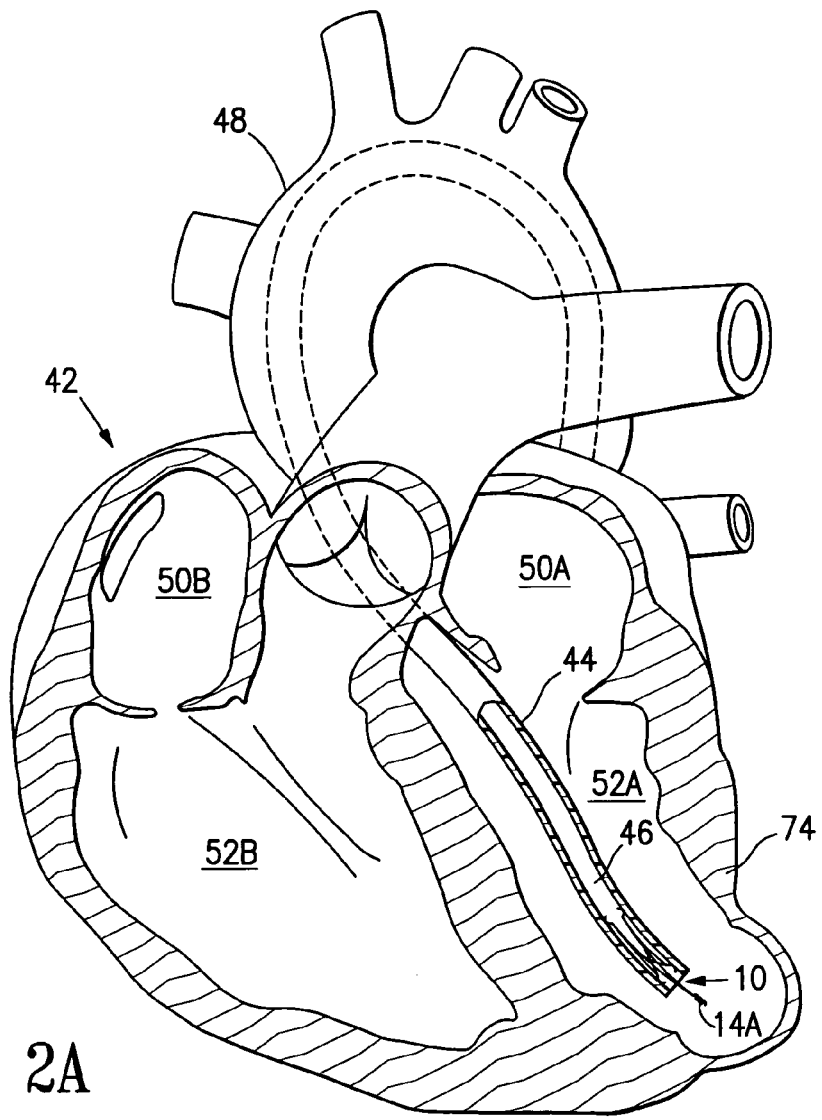
FIG. 2A is a cross-sectional side view of a heart, a catheter that is inserted into a left ventricle of the heart, and the device as it is packaged within an end of the catheter.

FIG. 2A illustrates the device 10 that is inserted into a heart 42 by means of a catheter 44. The device 10 is collapsed and is inserted into an end of the catheter 44. The axis 24, shown vertically in FIGS. 1A and 1B, now extends along an axis of an elongated tubular passage 46 in the catheter 44. The device 10 is packaged with the distal anchoring screw 14A protruding from the end of the catheter 44. The catheter 44 is non-invasively steered through the aorta 48 and the aortic valve (not shown) into the left ventricle 52A of the heart 42. The other chambers of the heart 42 are the right ventricle 52B, the left atrium 50A, and the right atrium 50B.

Figure 2B:
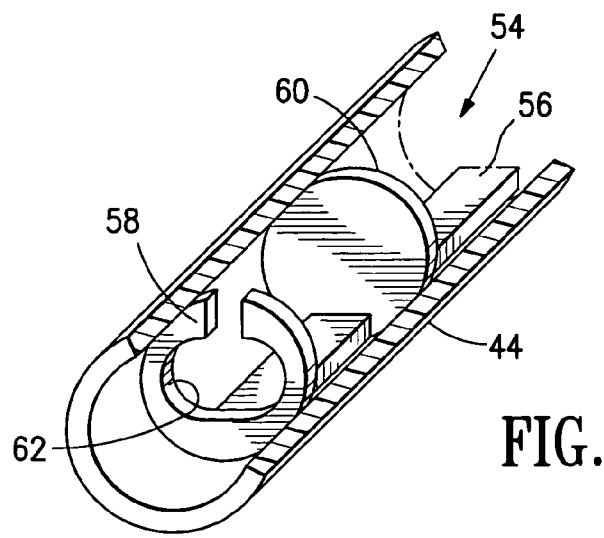
FIG. 2B is a perspective view illustrating a device manipulating apparatus within the end of the catheter.

As shown in FIG. 2B, a device manipulating apparatus 54 is disposed within the catheter 44. The apparatus 54 includes an elongated manipulator 56, a rotator piece 58, and a support piece 60. Only a distal portion of the elongated manipulator 56 is shown. A handle (not shown) is attached to a proximal portion of the elongated manipulator 56. The elongated manipulator 56 can bend to conform to the curved or bent shape of the catheter 44, but is relatively rigid against a torque about an elongated axis thereof. The rotator piece 58 is secured to an end of the elongated manipulator 56, and the support piece 60 is secured to the elongated manipulator 56 slightly proximal to the rotator piece 58. The rotator piece 58 has an internal device engaging formation 62. The device 10 is inserted into the formation 62 until proximal surfaces of the device 10 contact the support piece 60. The formation 62 conforms to an outer shape of the device 10, so that the device 10 rotates together with the rotator piece 58 when the rotator piece 58 is rotated by the elongated manipulator 56. The device 10 may be fed out of an end of the catheter 44 by the support piece 60 when the elongated manipulator 56 is advanced in an elongated direction of the catheter 44. The support piece 60 also prevents movement of the device 10 in an opposite direction into the catheter 44.

Figure 3A:
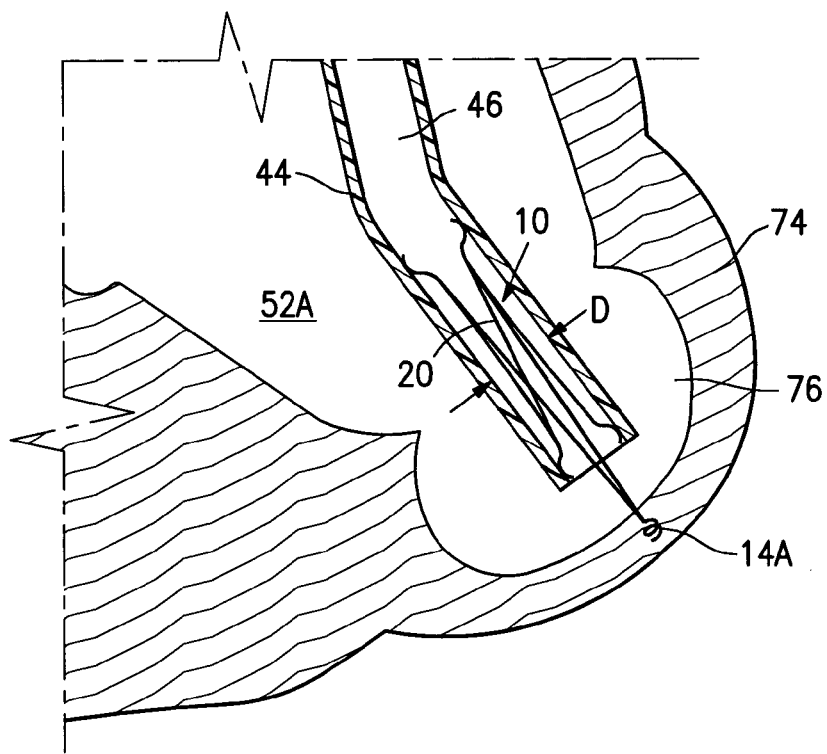
FIGS. 3A-3D illustrate how the device is secured to a myocardium of the heart.

Reference is now made to FIG. 3A. The myocardium 74 of the heart has formed an aneurysmic formation or bulge 76 out of the left ventricle 52A. A previous infarction, or cessation of blood supply, to the portion of the myocardium 74 now forming the bulge 76. Continuous exposure of the dyskinetic portion of the myocardium 74 to high pressures in the left ventricle 52A has caused the aneurysmic bulge 76.

The catheter 44 is steered so that the distal anchoring screw 14A contacts a base of the bulge 76. The catheter 44 is then rotated so that the distal anchoring screw 14A screws into the myocardium 74 at a target site the base of the bulge 76.

Figure 3B:
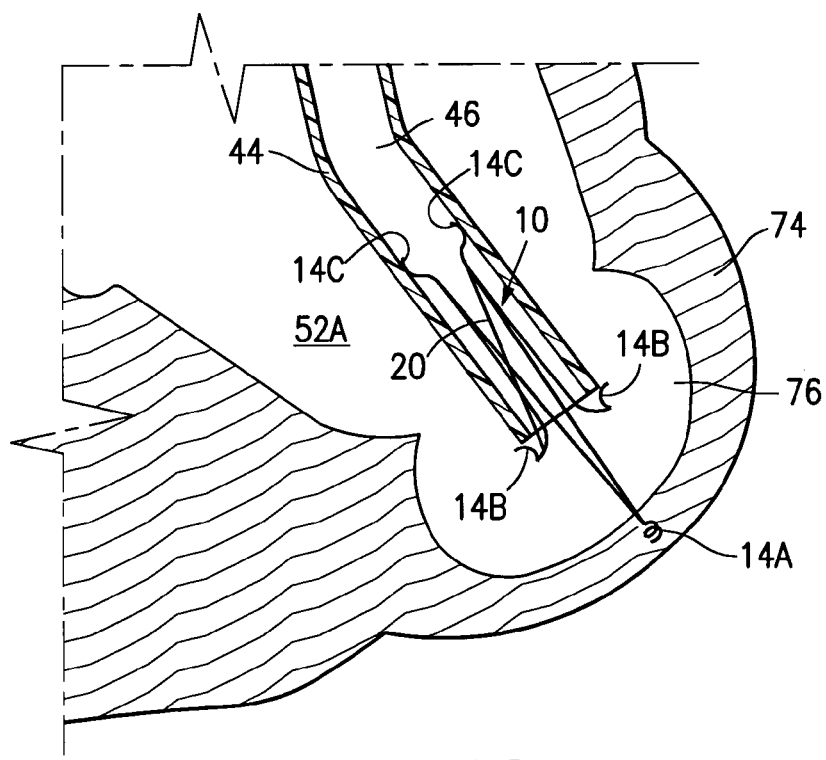

As shown in FIG. 3B, the catheter 44 is then retracted over the device 10, with the distal anchoring screw 14A anchoring the frame construction 12 to the myocardium 74 at the base of the bulge 76. The distal anchoring hooks 14B leave the catheter 44 as the catheter 44 is retracted, before the remainder of the device 10, and bend outwardly under spring action.

Figure 3C:
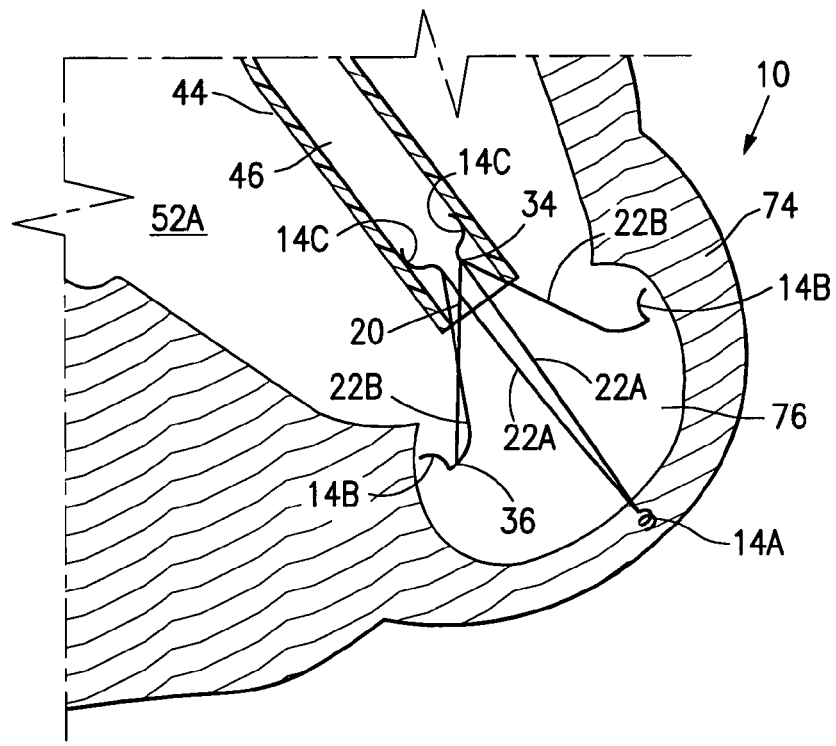

As shown in FIG. 3C, further withdrawal of the catheter 44 from the segments 22B causes the segments 22B to spring outwardly, and the distal anchoring hooks 14B to come into contact with the myocardium 74. The support frame 20 pivots away from its alignment with the center axis of the elongated tubular passage 46, and the proximal anchoring hooks 14C are at this stage still located within the elongated tubular passage 46.

Figure 3D:
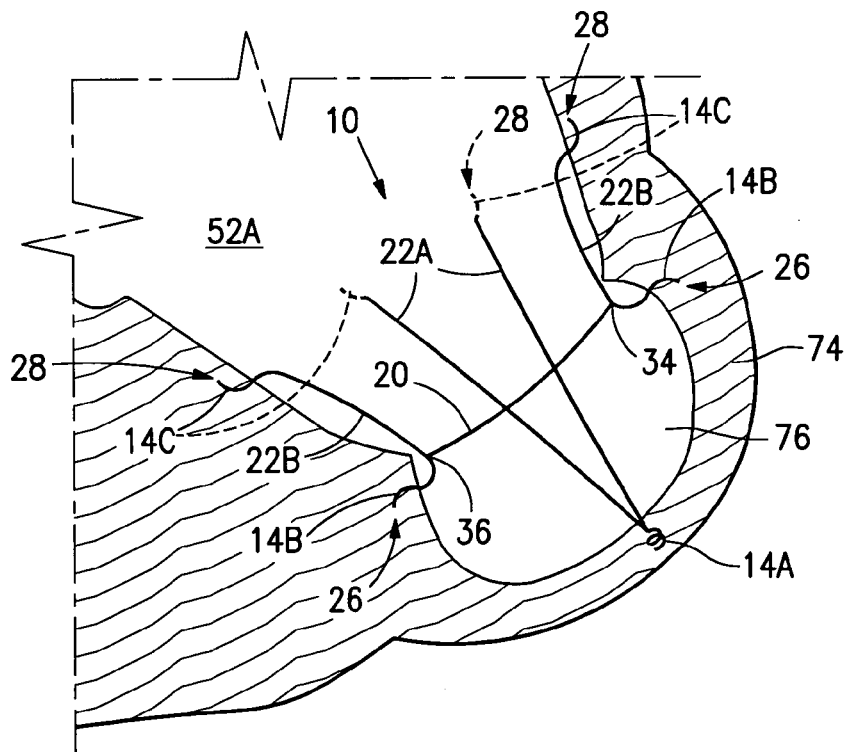

As shown in FIG. 3D, the catheter 44 is subsequently withdrawn from proximal anchoring hooks 14C. Proximal portions of the segments 22A and 22B spring outwardly after the proximal anchoring hooks 14C leave the tubular passage 46, so that the proximal anchoring hooks 14C move outwardly into contact with the myocardium 74. A proximal portion of each segment 22A or 22B pivots relative to a distal portion thereof. Pivoting of the segments 22B rotates the lower sharp ends 26 of the distal anchoring hooks 14B into the myocardium 74. Embedding of the distal anchoring hooks 14B into the myocardium 74 anchors the segments 22B to the myocardium 74. Beating of the heart 42 causes relative movement between the myocardium 74 and proximal anchoring hooks 14C, so that the upper sharp ends 28 may also penetrate the myocardium 74. The proximal anchoring hooks 14C are thereby also embedded into the myocardium 74, and anchor proximal portions of the segments 22A and 22B to the myocardium 74. Each segment 22A or 22B is near the myocardium 74 at all locations along the length of the respective segment 22A or 22B, and is anchored to the myocardium 74 through the anchoring formations 14.

The corners 34 of the support frame 20 slide along the segments 22B to which they are secured when the segments 22B rotate outwardly relative to one another. When comparing FIG. 3D with FIG. 3C, it can be seen that the support frame 20 is in a plane which is substantially at right angles with respect to the axis of the elongated tubular passage 46. The membrane 16 (FIG. 1C) unfolds and is supported on top of the support frame 20. The membrane 16 forms a division between the aneurysmic bulge 76 and a remainder of the left ventricle 52A.

After the device 10 is installed, the aneurysmic bulge 76, having been segregated from the remainder of the left ventricle 52A, eventually clots off behind the membrane 16, thereby effectively reducing the internal volume in the left ventricle 52A. Stretching of the portion of the myocardium 74 forming the aneurysmic bulge 76 is also effectively eliminated. By blocking off a portion of the left ventricle 52A not contributing to pumping during a systolic portion of a pump cycle, properly functioning portions of the myocardium 74 can contract normally and use up a normal amount of oxygen. By reducing the amount of oxygen uptake during a given period of time, properly functioning portions of the myocardium 74 are not exhausted and can continue to function properly. Cardiac output increases and the likelihood of congestive heart failure is reduced.

Figure 4A:
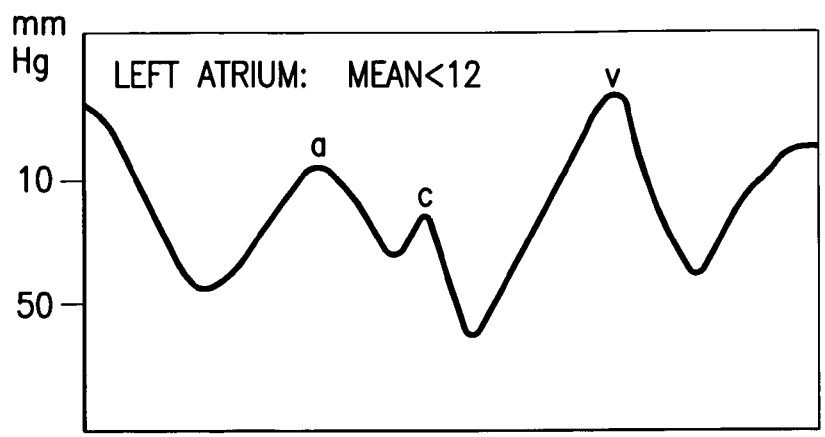
FIGS. 4A-4B are graphs illustrating the pressures within the left atrium and the left ventricle, respectively.
Figure 4B:
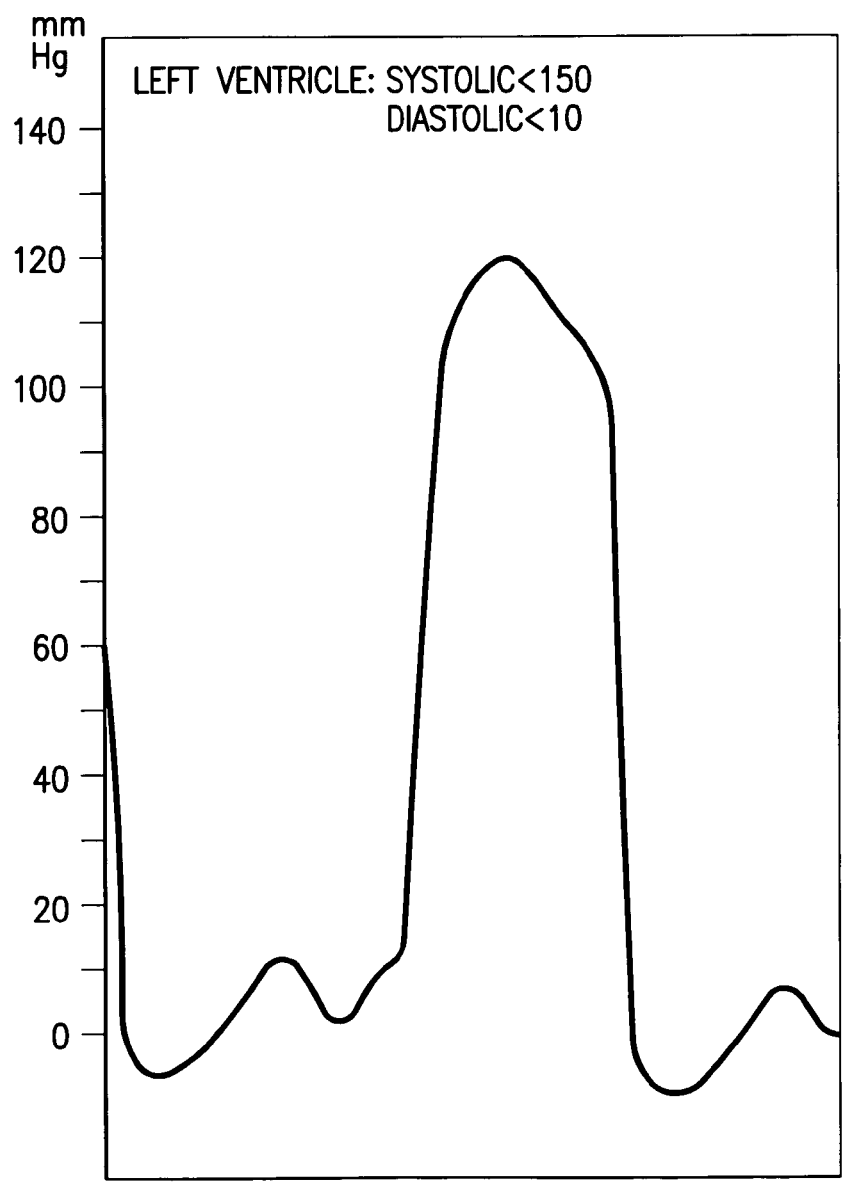

FIGS. 4A and 4B illustrate pressures within the left atrium 50 and the left ventricle 52A, respectively, of a healthy human being. It can be seen that the peak left ventricular pressure, i.e., the pressure in the left ventricle 52A during the systolic portion, reaches approximately 120 mm Hg. This pressure acts directly on the membrane 16. It can be assumed that the pressure on an opposing side of the membrane 16, i.e., the side of the aneurysmic bulge 76, is close to zero. The support frame 20 supports the sheet 16 at a sufficient number of locations and is sufficiently strong to prevent the membrane 16 from collapsing during peak systolic pressure. An peak pressure in the region of 50 to 60 mm Hg for a sustained period of a few hours is generally regarded as being incompatible with life.

In the given example, there are a total of 31 anchoring formations 14, including the distal anchoring screw 14A, 14 distal anchoring hooks 14B, and 16 proximal anchoring hooks 14C. The large number of anchoring formations 14 ensure proper anchoring to the myocardium 74. The large number of anchoring formations 14 also allows for positioning of the membrane 16 at a select location within the left ventricle 52A and at a select angle and within a select plane relative to the myocardium 74. The anchoring formations 14, and in particular the anchoring hooks 14B and 14C, their shape, orientation, and placement, are thus uniquely suited for anchoring of the frame construction 12, especially when compared with other anchoring formations such as pins, clamps, staples, screws, and surgical thread. What should also be noted is that the anchoring formations 14 penetrate through only a portion of the myocardium 74, and thus do not damage the pericardium. What should further be noted is that none of the anchoring formations 14 or other components of the device 10 can bump against the myocardium 74, to avoid electrostimulation of the myocardium 74 that can lead to arrhythmias.

Figure 5A:
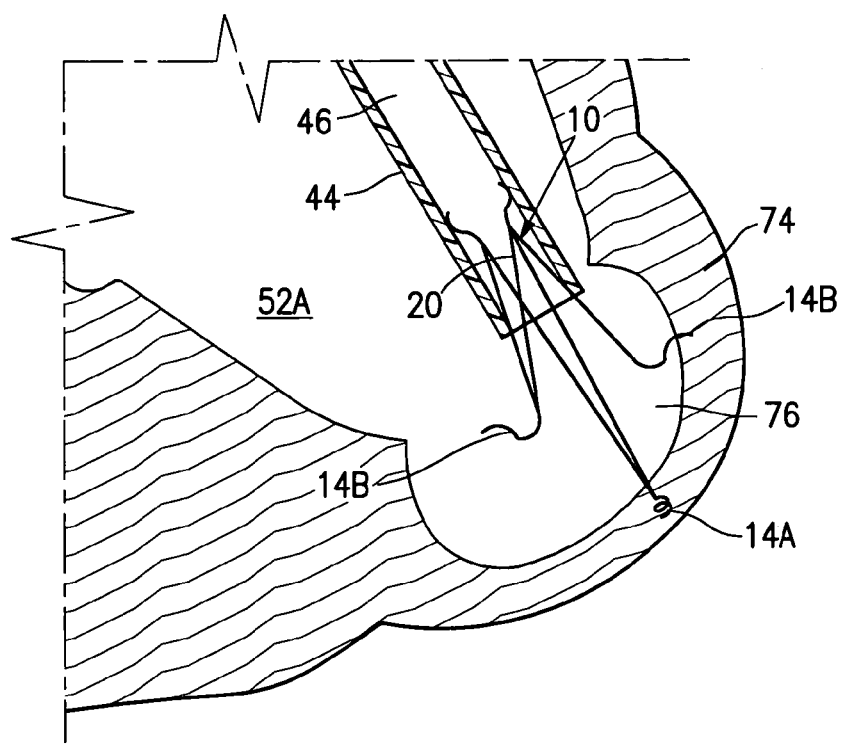
FIGS. 5A-5C illustrate how the device can be mounted with the support frame to support the membrane in a different plane.
Figure 5B:
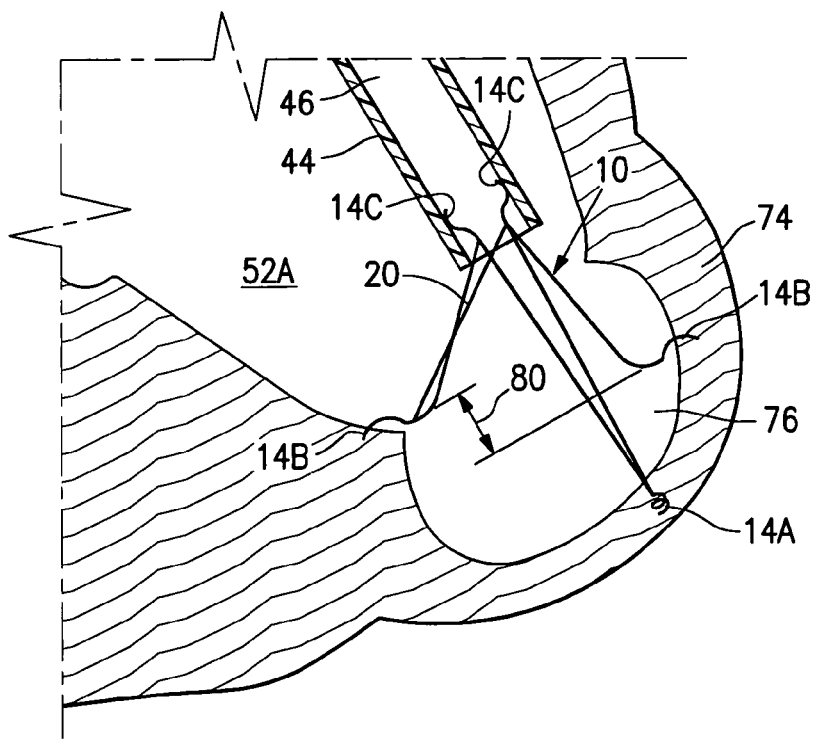
Figure 5C:
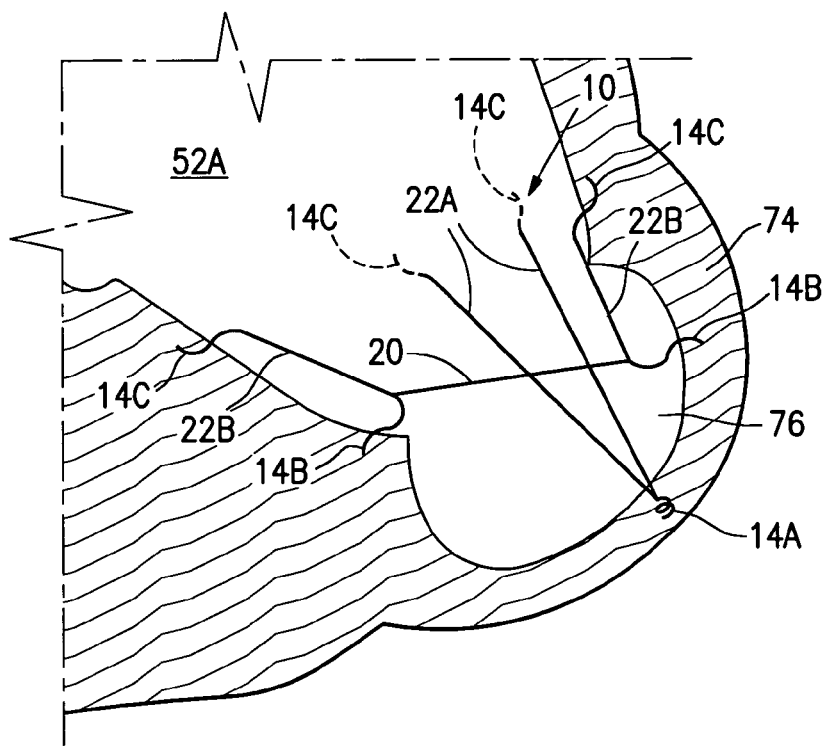

FIGS. 5A, 5B, and 5C illustrate one manner in which the support frame 20 and the membrane 16 can be positioned at a select angle relative to the myocardium 74. When comparing FIG. 5A with FIG. 3C, it can be seen that the catheter 44 is positioned closer to a right side (as viewed) of the myocardium 74. The distal anchoring hooks 14B on the right engage with the myocardium 74 before the distal anchoring hooks 14B on the left engage with the myocardium 74. Further withdrawal of the catheter 44, as shown in FIG. 5B, results in engagement of the distal anchoring hooks 14B on the left with the myocardium 74 at a location which is displaced by an offset distance 80 in a direction of an axis of the elongated tubular passage 46. When comparing FIG. 5C with FIG. 5B, it can be seen that, due to the offset distance 80, the support frame 20 is eventually at an angle of approximately 60° relative to the axis of the elongated tubular passage 46. Although not blocking a mouth of the aneurysmic bulge 76, this serves to illustrate that the membrane 16 can be positioned in different select planes, as may be required, due to the flexibility of the frame construction 12 and various virtual triangles that are formed by connecting locations where the anchoring formations 14 anchor to the myocardium 74.

Referring again to FIGS. 1A, 1C, and 3A, the main frame 18 has a vertical height H1, a height from the distal anchoring hooks 14B to the proximal anchoring hooks 14C H2, the membrane 16 has a width W, and the elongated tubular passage 46 has a diameter D. These dimensions can be modified according to requirement, and the following table lists a number of examples:

| H1 | H2 | W | D |
|---|---|---|---|
| 6 cm | 3 cm | 2.5 cm | 1 cm |
| 7 cm | 4 cm | 3 cm | 1.2 cm |
| 8 cm | 5 cm | 4 cm | 1.5 cm |
| 8.5 cm | 5.5 cm | 5 cm | 2 cm |
| 9.5 cm | 6 cm | 6 cm | 2.2 cm |
| 9.5 cm | 8 cm | 7 cm | 2.6 cm |

The first row in the table lists the dimensions for the device 10 hereinbefore described which is used for blocking a relatively small aneurysmic bulge 76. Larger aneurysmic bulges can be blocked using slightly larger devices. As mentioned, certain diseases may cause general enlargement of endocardial cavities of a heart without necessarily creating a specific identifiable bulge. Larger devices can be used to block portions of these enlarged endocardial cavities. In such cases, it may also be possible to use two devices in a side-by-side arrangement or with their membranes overlapping one another.

Figure 6:
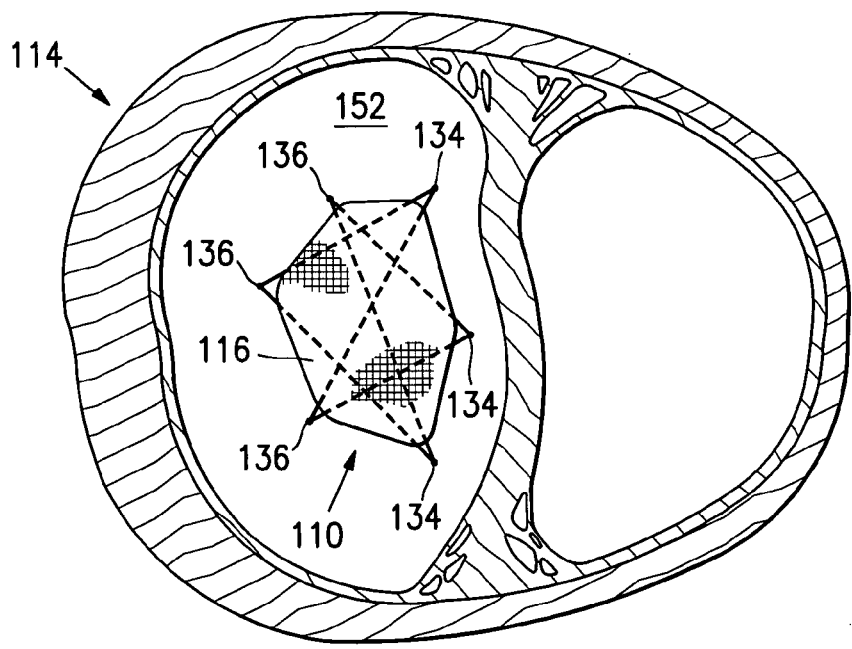
FIG. 6 is a top plan view illustrating a larger device, according to another embodiment of the invention, mounted in a lower portion within a left ventricle of a heart.

FIG. 6 illustrates one such a larger device 110 that is inserted in the bottom of the left ventricle 152 of a heart 114. The main frame (not shown) of the device 110 is formed into a non-circular shape, so that an outline formed by corners 134 and 136 of a support frame of the device define a non-circular shape. A membrane 116 mounted on top of the support frame also defines a non-circular shape. The shape of the membrane 116 conforms approximately to a non-circular D-shape of the left ventricle 152 at a height where the membrane 116 is positioned. The same device 110 can be deformed into various different shapes, according to requirement.

Figure 7A:
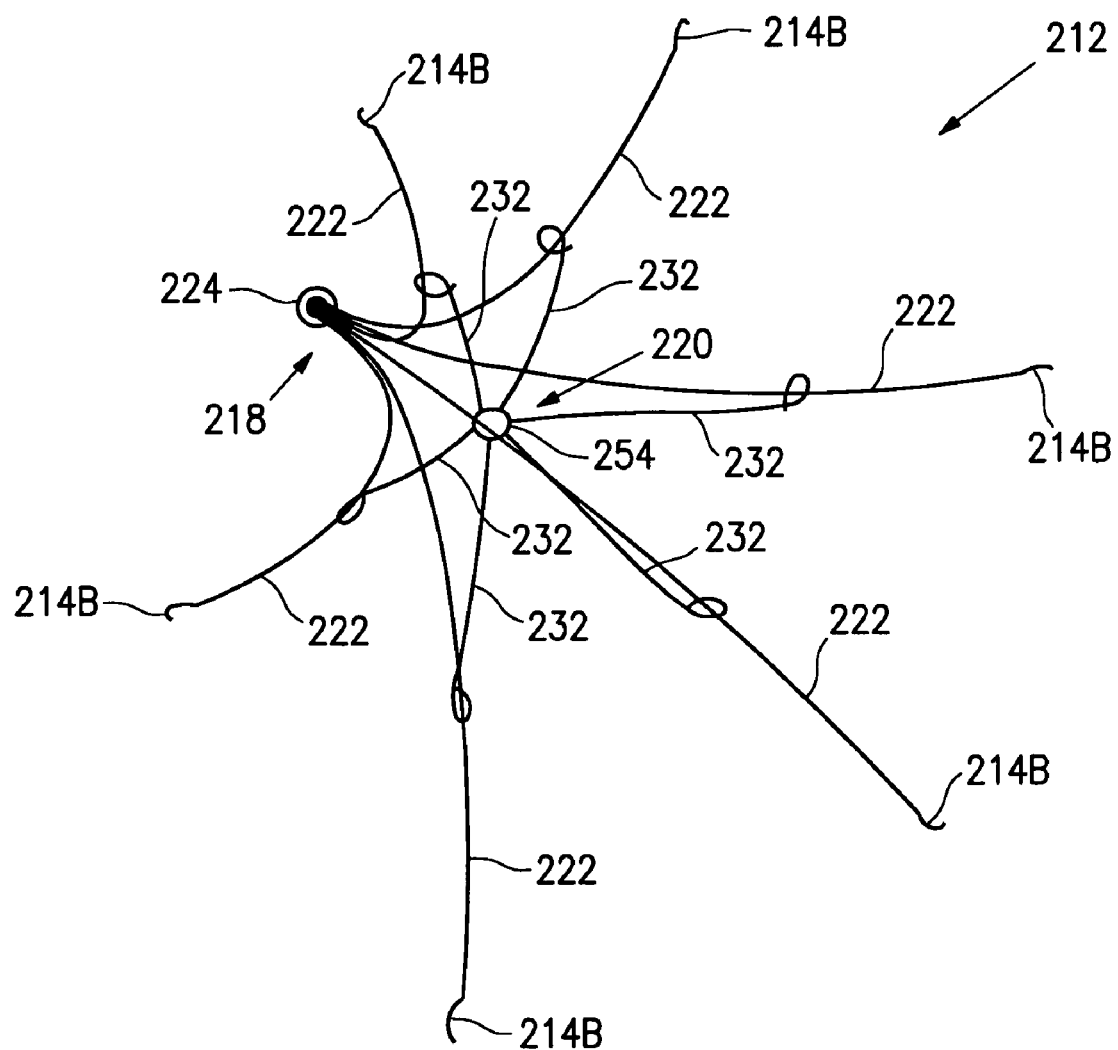
FIGS. 7A-7B are perspective views from different sides, illustrating components of a device according to a further embodiment of the invention.
Figure 7B:
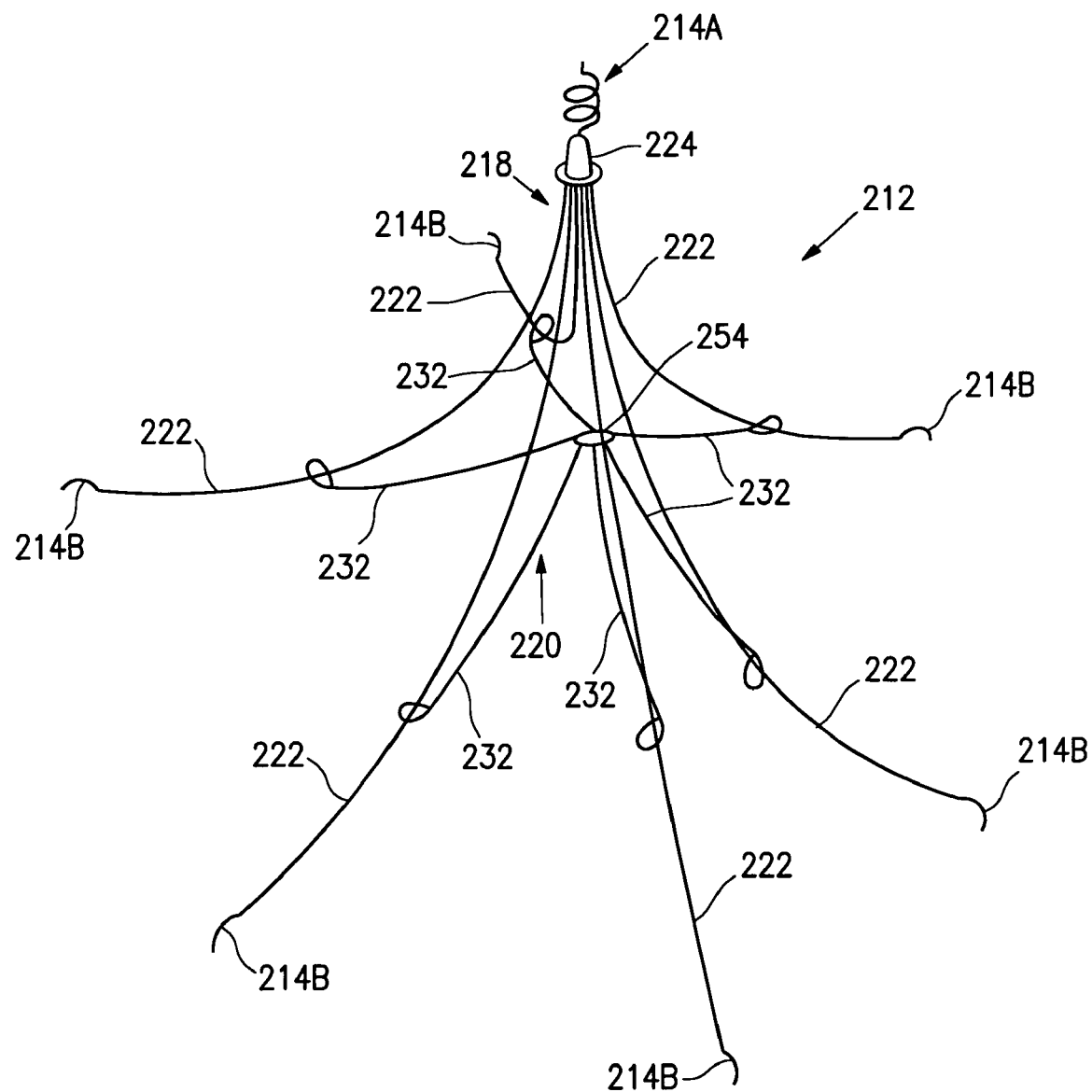

FIGS. 7A and 7B illustrate a frame construction 212 and anchoring formations 214 of a device according to an alternative embodiment of the invention. The frame construction 212 includes a main frame 218 and a support frame 220. The main frame 218 has a plurality of segments 222 having distal ends connected to one another at a common location 224. Proximal portions of the segments 222 can collapse toward one another and spring outwardly away from one another. The anchoring formations 214 include a distal anchoring screw 214A secured at the common location 224, and proximal anchoring hooks 214B on proximal ends of the segments 222. The support frame 220 includes a plurality of elements 232. The elements 232 have ends that are pivotally connected to one another at a common location 254. An opposing end of each element 232 is slidably secured to a respective one of the segments 222. The manner in which the segments 222 of the main frame 218 collapse is simultaneously replicated by the manner in which the elements 232 of the support frame 220 collapse. In use, the distal anchoring screw 214A is first screwed into a myocardium. A catheter is then withdrawn from the frame construction 212. Once the catheter is entirely removed from the frame construction 212, the proximal anchoring hooks 214B spring outwardly and embed themselves into the myocardium. The support frame 220 simultaneously moves from its collapsed condition into its expanded condition. A membrane (not shown) is secured to, unfolded by, and supported by the support frame 220.

Figure 8:
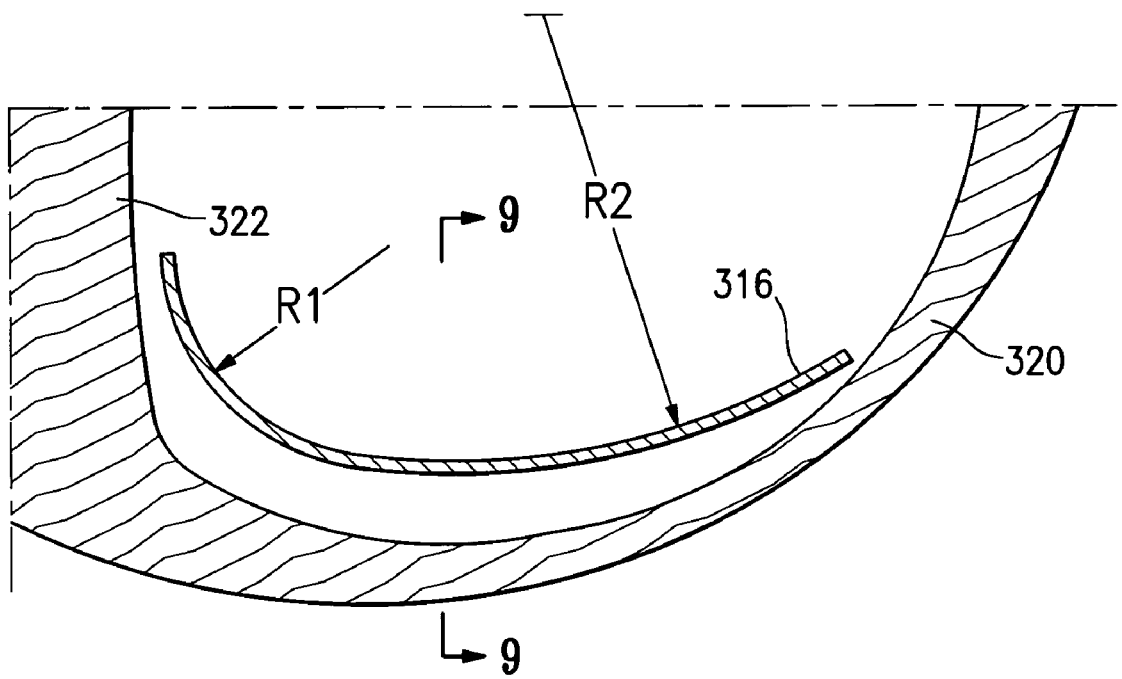
FIG. 8 is a cross-sectional side view illustrating a sheet that is curved to substantially conform to an inner wall of a heart.
Figure 9:
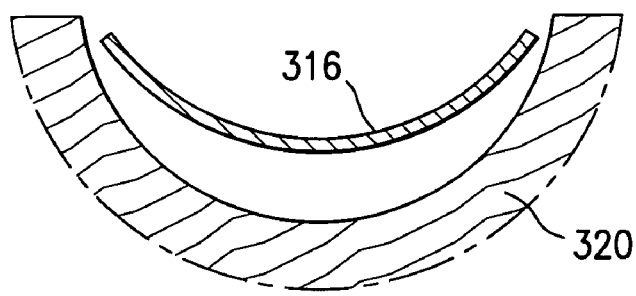
FIG. 9 is a cross-sectional end view on 9-9 in FIG. 8.

The support frame of a device may be shaped so that a membrane attached to the support frame has a desired shape. FIGS. 8 and 9, for example, illustrate a membrane 316 that conforms approximately to a shape defined by an anterior wall 320 and a septum 322 of a heart. As shown in FIG. 8, the membrane 316 has a portion on the left having a radius R1 and a portion on the right having a radius R2 which is a multiple of the radius R1. The sheet 316 material may be formed to have more than two radii of curvature. Referring to FIG. 9, it can be seen that the membrane 316 is curved also when viewed on 9-9 in FIG. 8. The curved shape of the membrane 316 allows the membrane 316 to block off larger portions of the anterior wall 320 and the septum 322 without reducing the internal volume of the left ventricle by too great a degree.

Figure 10:
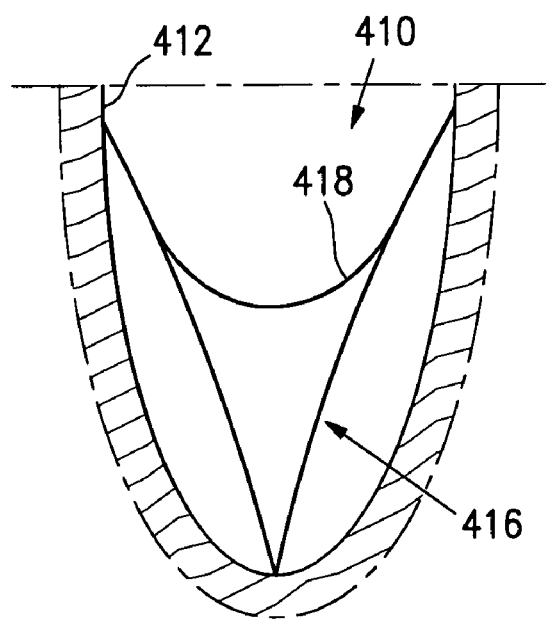
FIG. 10 is a cross-sectional side view illustrating a device that is used for closing off a small ventricle of a heart.
Figure 11:
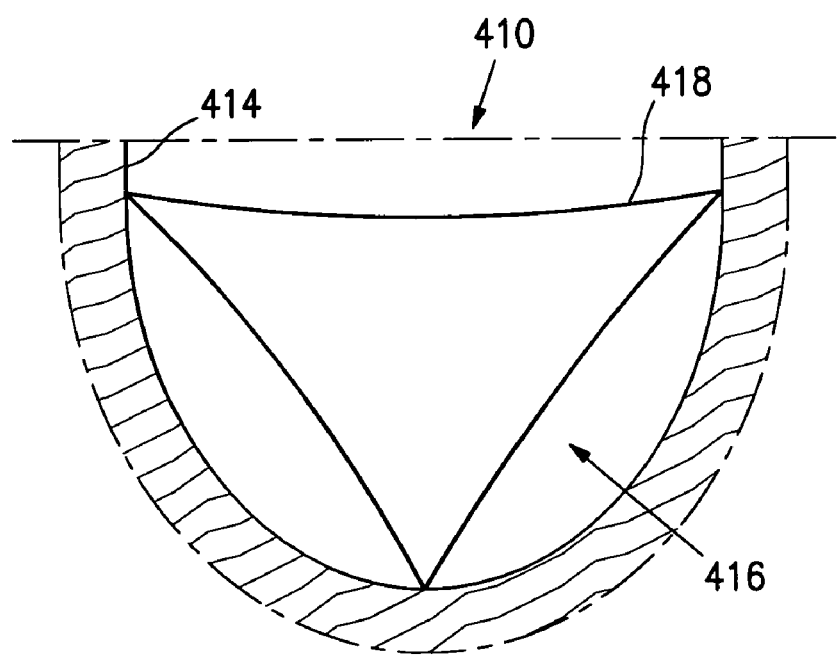
FIG. 11 is a cross-sectional side view illustrating the same device as in FIG. 10, used for closing off a large ventricle of a heart.

It may also be possible to use the same device to block off either large or small cavities. FIGS. 10 and 11 illustrate the same device 410 used for closing off a small ventricle 412 and a large ventricle 414, respectively. As in, for example, the embodiment described with reference to FIGS. 7A and 7B, the device 410 has a frame construction 416 that can spring outwardly, and a membrane 418 secured and expanded by the frame construction 416. The frame construction 416 springs out more in FIG. 11 than in FIG. 10, and the membrane 416 is accordingly unfolded into a larger cross-sectional shape.

The support frame and anchoring formations of, for example, the device illustrated in FIG. 1A may be used for other purposes instead of or in addition to supporting a membrane as described. The frame construction 18 provides an electrically conductive path that can be used for left ventricular pacing. For example, one of the proximal anchoring hooks 14C may engage with and be sufficiently long to penetrate from a left ventricle through a septum into a right ventricle of a heart. A terminal of a pacemaker can then be inserted into the right ventricle and connected to the hook that penetrates through the septum. Electric current can conduct between the terminal of the pacemaker through the main frame 18 to other ones of the anchoring formations 14 connected to the myocardium of the left ventricle. The frame construction 12 also provides a strong support for mounting components that can be used for other purposes, such as an annulus component that can be positioned around the mitral valve, or a component that is used for reshaping a papillary muscle. The device 10 can also be used for delivering of drugs, proteins, stem cells, etc. to the heart.

Figure 12:
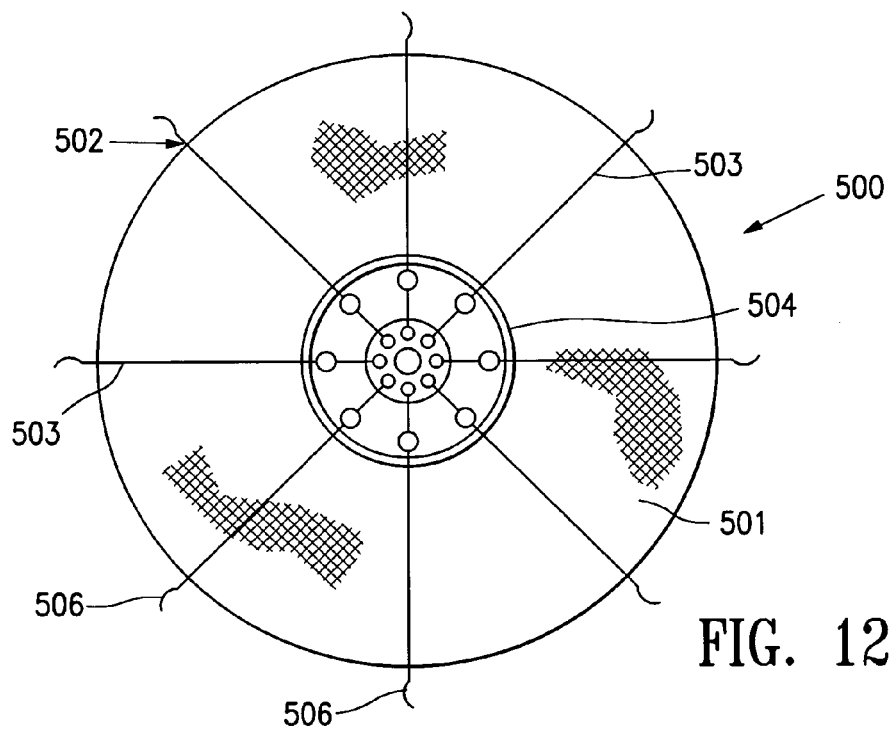
FIG. 12 is a top plan view of a partitioning device embodying features of the invention.
Figure 13:
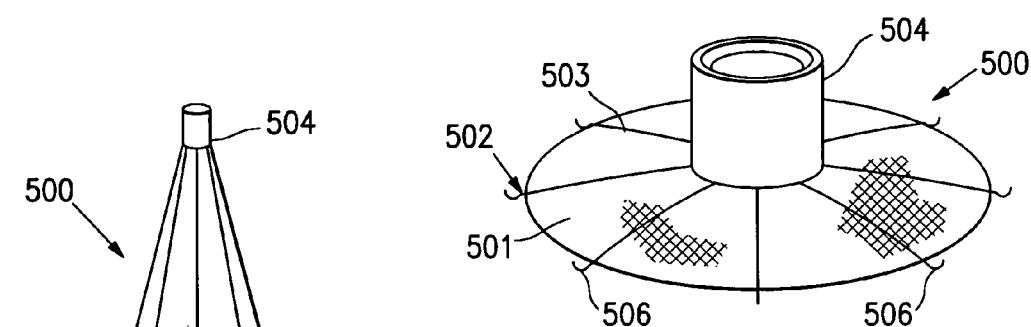
FIG. 13 is an isometric view of the device of FIG. 12 in its extended state.
Figure 14:
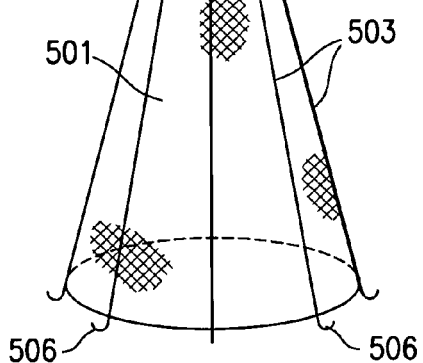
FIG. 14 is an isometric view of the device of FIG. 12 in a partially collapsed state.

In the embodiment illustrated in FIG. 12, a partitioning device 500 includes a generally circular membrane 501 which is mounted on a collapsible frame 502. The frame 502 has a plurality of stays 503 which extend radially from a central hub 504 for movement between the extended position shown in FIGS. 12 and 13 and a collapsed position as shown in FIG. 14. The stays 503 are connected to the hub 504 in such a way that rotation of the hub moves the stays between their extended and collapsed positions. Hooks or barbs 506 are provided at the outer ends of the stays for, attaching the device to the walls of an organ, with the membrane in its extended state.

Figure 15:
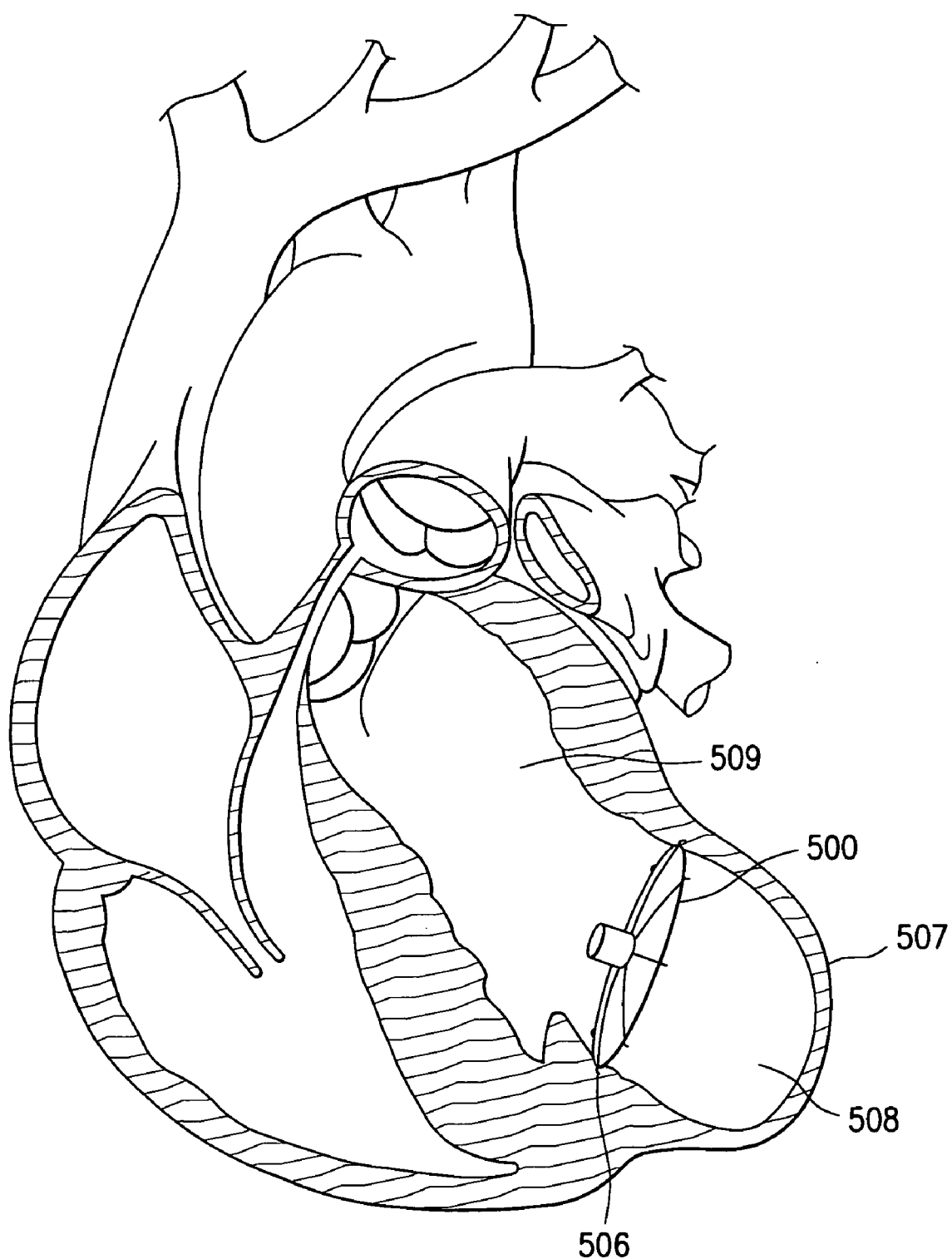
FIG. 15 illustrates the use of a device embodying features embodying features of the invention within a chamber of a patient's heart.

Then the device 500 is deployed in an organ, the membrane 501 divides the organ into two separate compartments. Those compartments will be determined by the physician and typically will consist of a functional compartment and a nonfunctional compartment. For example, in the case of a left ventricular aneurysm (an enlargement of one small part of the left ventricular myocardium), the device is positioned at the mouth of the aneurysm 507, as illustrated in FIG. 15, to divide the left ventricle into a nonfunctional part 508 consisting of the aneurysm itself, and a functional part 509 consisting of the remainder of the left ventricle. The elimination of communication between the aneurysm and the functional part of the ventricle will significantly improve the overall performance of the left ventricle. This procedure can be performed either during open chest surgery or by less invasive techniques such as laparoscopic or percutaneous delivery of the device to the inside of the ventricle.

In the case of congestive heart failure, the ventricle can similarly be divided into functional and nonfunctional parts, with improved overall ventricular performance. The elimination of one portion of the enlarged heart will prevent further cardiac enlargement and provide improved performance.

In the case of the stomach, the stomach could be divided into a nonfunctional part, i.e. the part which does not participate in digestion, and the remainder of the stomach which includes normal digestive processes.

The membrane is closely attached to the walls of the organ in order to prevent any communication between the two compartments. It can be elastic, non-elastic, non-porous, non-thrombogenic, and/or biocompatible. In one presently preferred embodiment, the membrane is fabricated of a mesh of elastin fibers (i.e. elastin proteins or a synthetic material) chosen to provide tensile strength and flexibility. The membrane can also have living cells (e.g., endothelial cells, myocytes, smooth muscle cells, or stem cells) and/or certain bioactive substances, such as heparin, on its surface.

In other embodiments, the membrane 501 can be rigid, or capable of changing size and shape to accommodate the size and shape of the organ. It can also be composed of hydrogels that change into a tendon-like structure and/or a bioresorbable material. It can also include a protein which will serve to attract the patient's own cells that will turn into myocytes and become a new myocardium.

As illustrated in FIGS. 16A-16D partitioning device 500 can be deployed with an instrument 511 which has an elongated tubular body 512. The device is carried within the tube in a collapsed state toward the distal end of the instrument. An operating rod 513 extends axially within the tubular body and is threadedly connected to hub 504 for advancing the device from the tubular body and rotating the hub to-extend the membrane. A control knob 514 is provided at the proximal end of the operating rod.

Figure 16A:
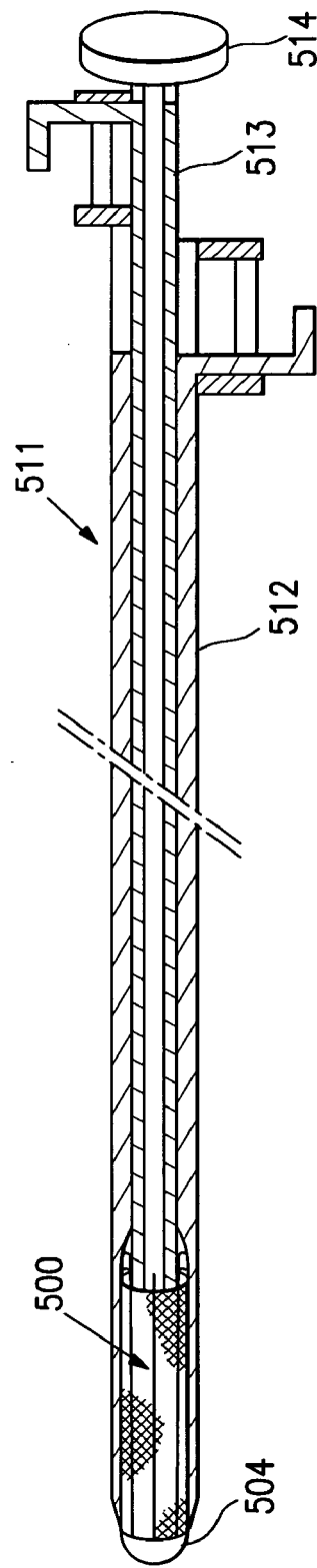
FIGS. 16A 16D are operational views, partly broken away, illustrating deployment of the device of FIG. 12 through a tubular instrument.
Figure 16B:
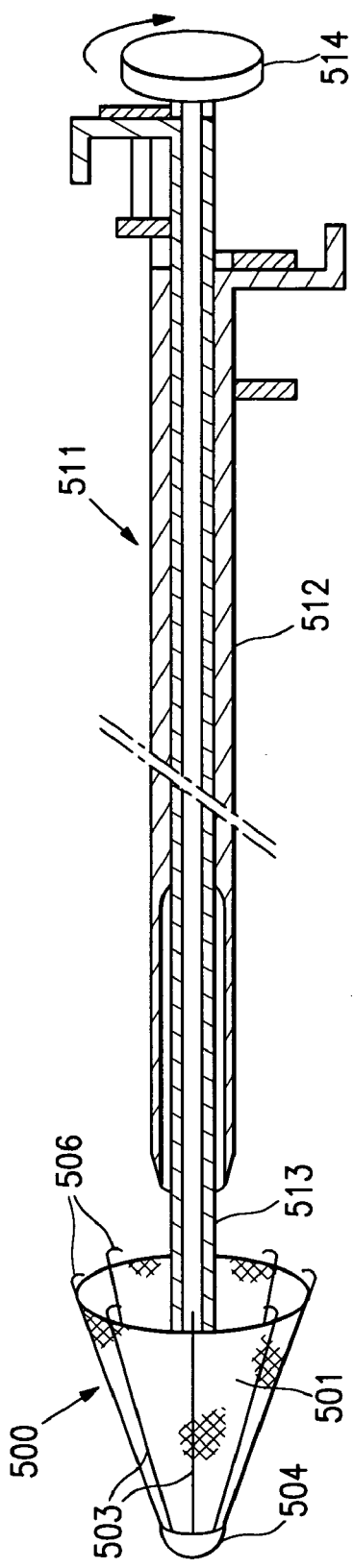

In operation, the instrument is inserted into the body of the patient, and operating rod 513 is moved forward to advance the partitioning device from the distal end of tubular body 512. As the device is moving forward, control knob is turned in a clockwise direction to extend the membrane, as illustrated in FIG. 16B. The advancement and expansion continues until the membrane reaches its fully extended position, as illustrated in FIG. 16C. Once barbs 506 have been engaged with the walls of the organ, the control knob is turned in counterclockwise direction to disengage the operating rod from the hub, as illustrated in FIG. 16D, and the instrument is withdrawn from the body of the patient.

Figure 17:
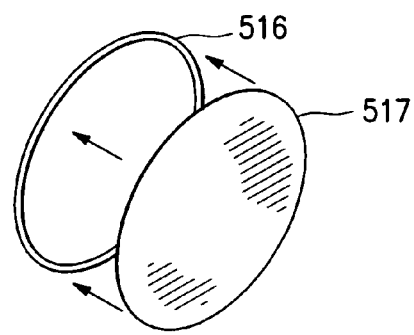
FIG. 17 is an isometric view of another device embodying features of the invention.

In the embodiment illustrated in FIG. 17, the partitioning device consists of a scaffold or ring 516 which is attached to the walls of the organ first, and a membrane 517 which is attached to the ring after the ring is in place. The scaffold has means such as mechanical devices (e.g. barbs or hooks) or an adhesive for attaching it to the walls of the organ and to the membrane. Both the scaffold and the membrane are collapsible, and can be introduced into the hollow organ through tubular devices such as an endoscope, a thoracoscope, or a catheter.

The partitioning device can be implanted in a number of ways. It can, for example, be implanted by a surgeon during a surgical procedure. It can also be implanted through an endoscope or a laparoscope during a laparoscopic procedure. Similarly, it can be implanted through a thoracoscope during a thoracoscopic procedure, and it can be delivered to the inside of an organ through a long tubular device such as a catheter, either percutaneously, orally, or by some other minimally invasive approach.

Figure 18:
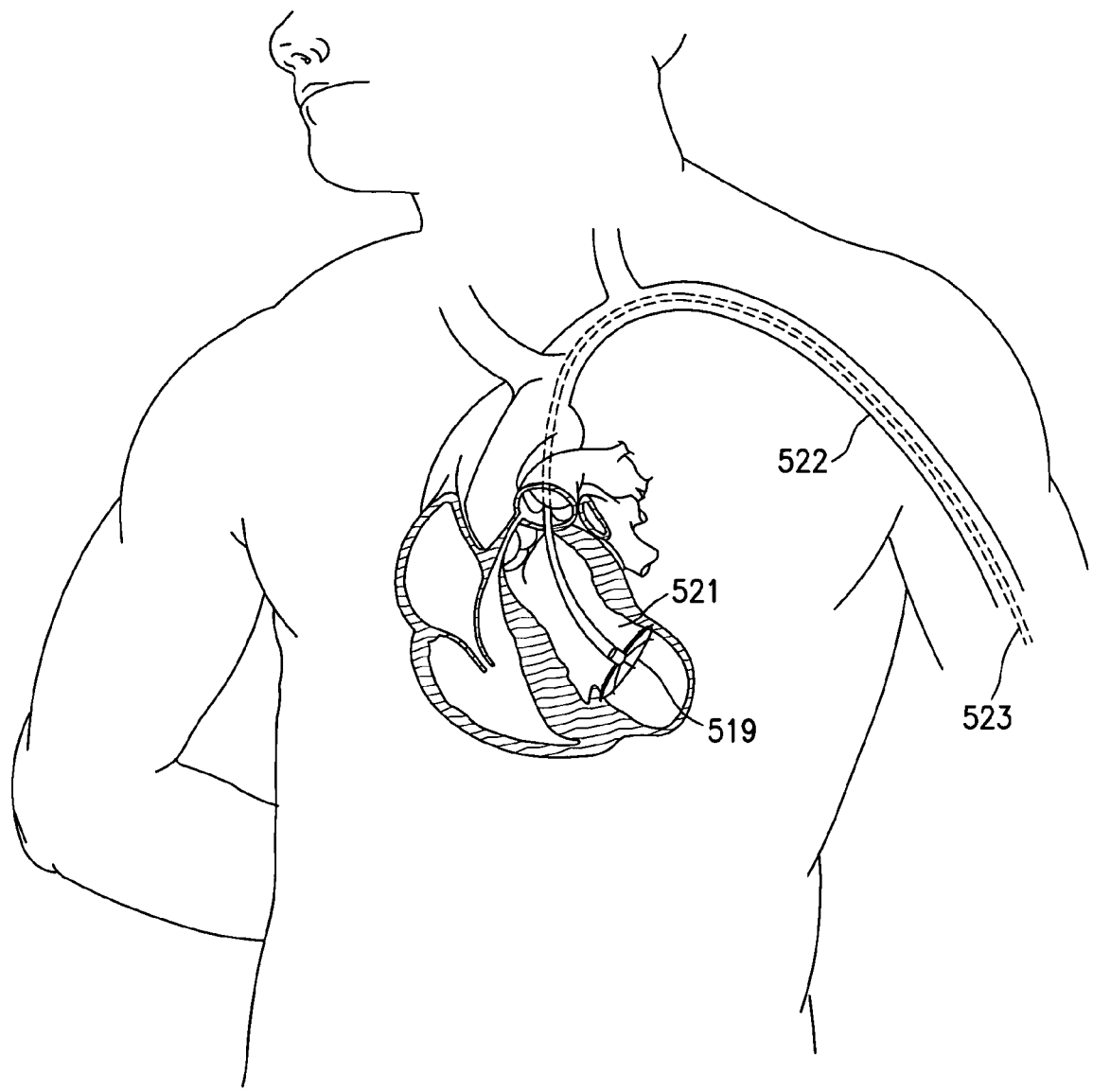
FIG. 18 illustrates the percutaneous delivery of an implantable device having features of the invention.

FIG. 18 illustrates the percutaneous insertion of a partitioning device 519 into a chamber of the heart 521 through the brachial artery 522. In this embodiment, a catheter 523 is passed through the artery and into the heart, and the partitioning device is inserted and deployed through the catheter. The catheter preferably has a mesh-like structure to prevent the occurrence of an embolism during the procedure.

Figure 19:
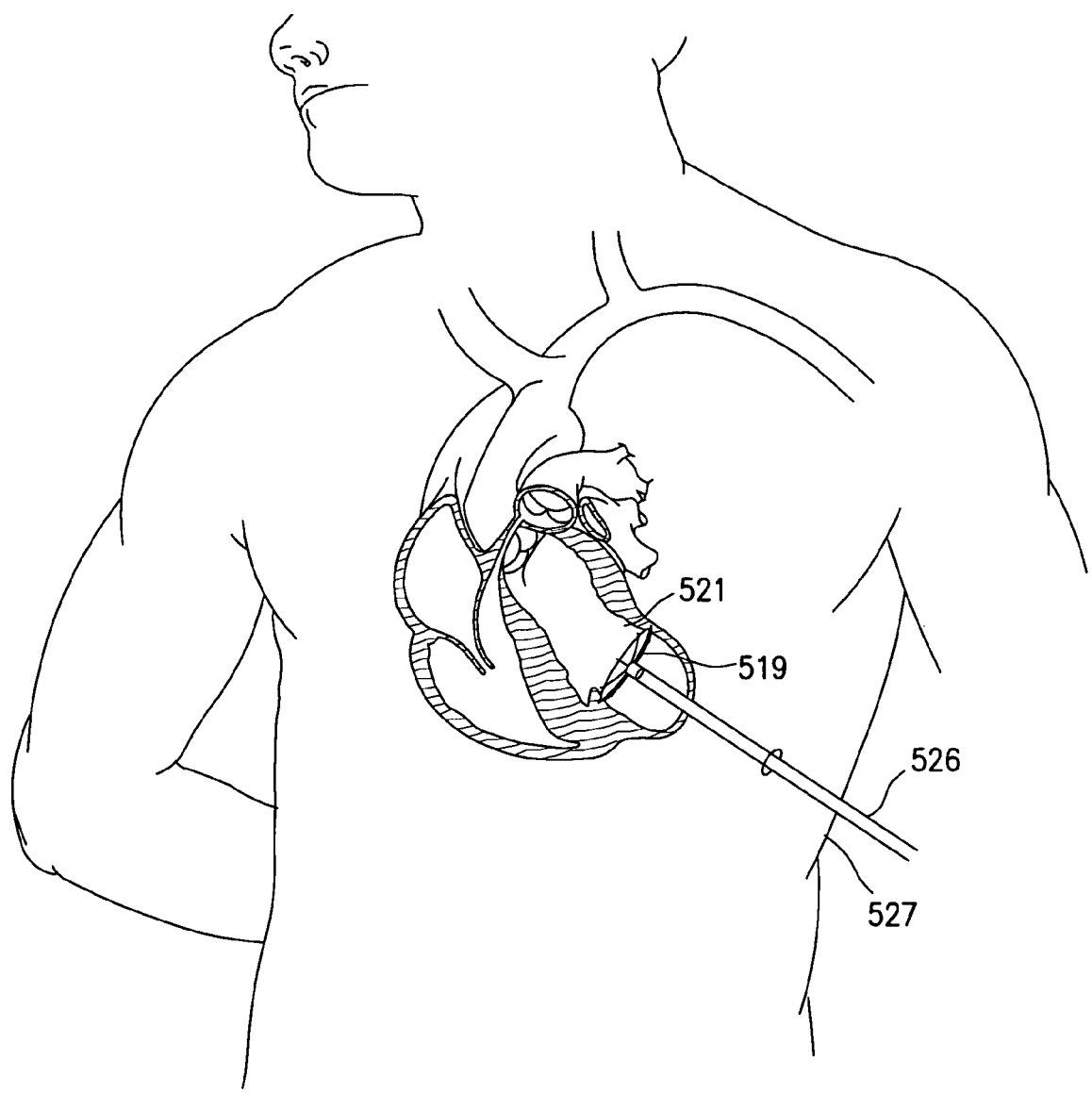
FIG. 19 illustrates the transthoracic delivery of an implantable device embodying features of the invention.

FIG. 19 illustrates the thoracoscopic placement of a partitioning device 519 in heart chamber 521. In this embodiment, the device is introduced and deployed through a thoracoscope 526 which is inserted into the patient's body through his thorax 527.

Figure 20:
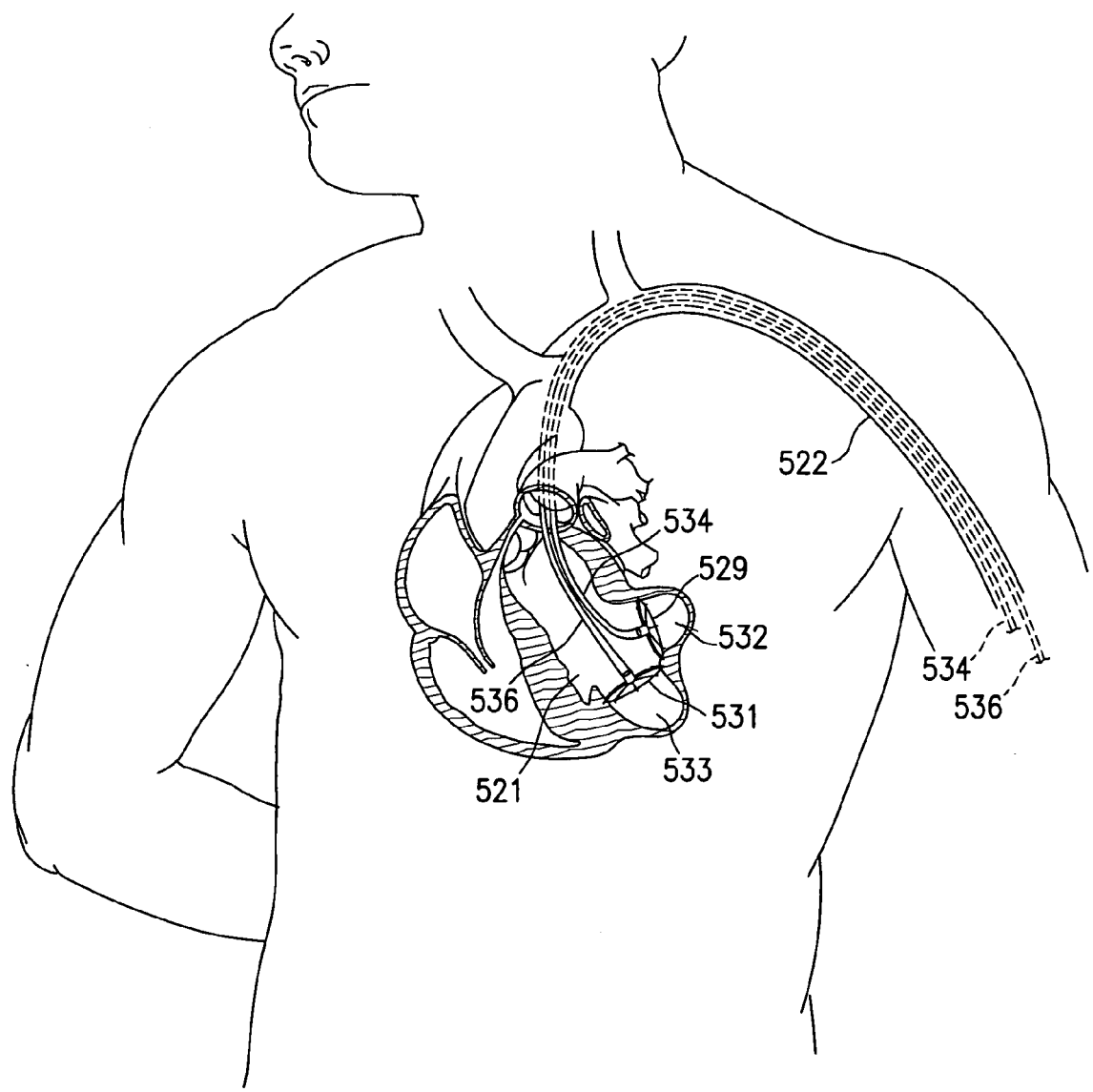
FIG. 20 is a view similar to FIG. 18, illustrating the percutaneous delivery of two devices embodying features of the invention to treat a ventricular aneurysm and an enlarged ventricle simultaneously.

If desired, more than one partitioning device can be employed, e.g. to treat more than one condition in an organ. FIG. 20, for example, illustrates the use of two percutaneously inserted membranes 549, 551 in the simultaneous treatment of a ventricular aneurysm 552 and an enlarged ventricle 553. In this particular embodiment, the membranes are introduced into the ventricle through two separate catheters 554, 556 which pass through the brachial artery. Alternatively, they can be introduced either simultaneously of successively through a single catheter, if desired.

Figure 21:
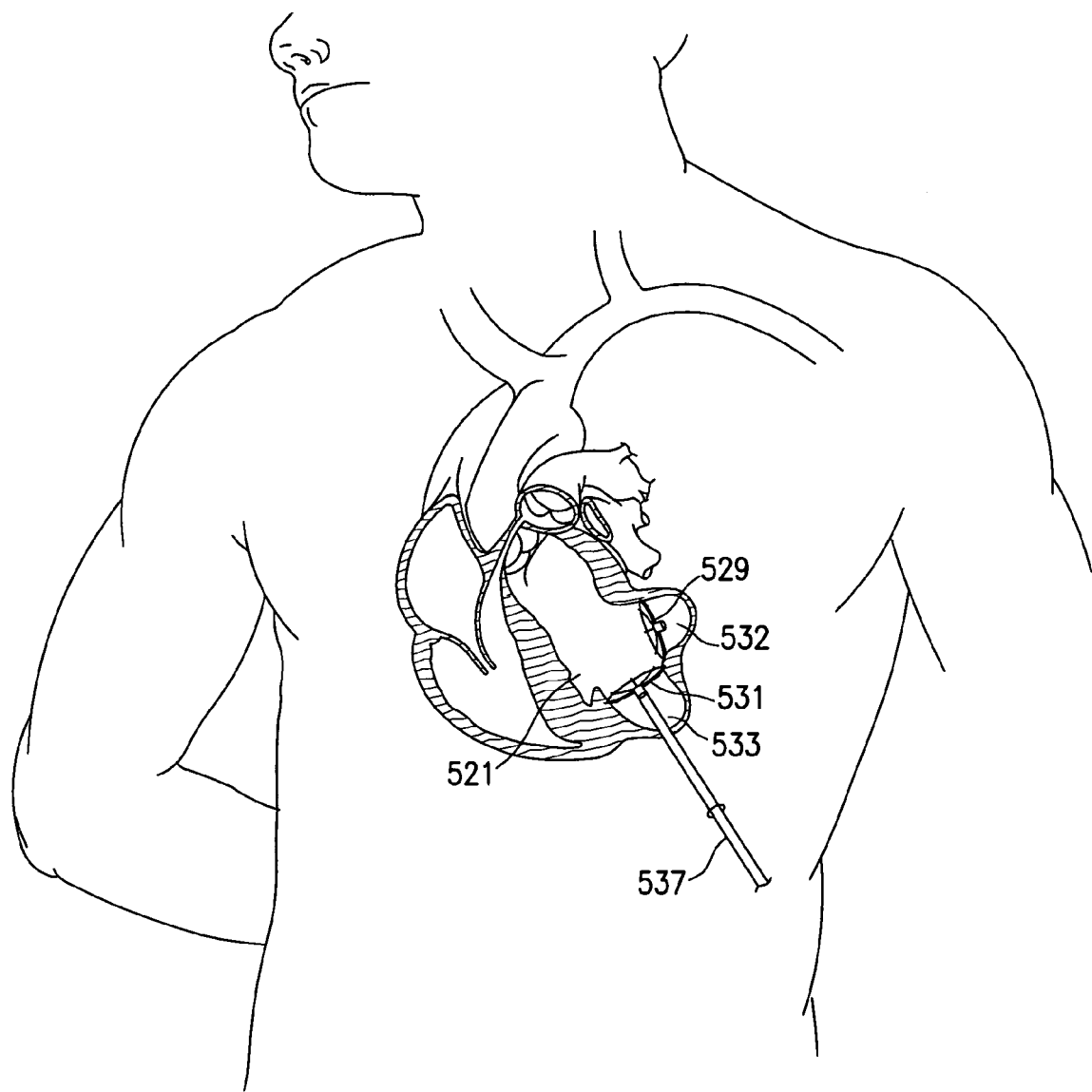
FIG. 21 is a view similar to FIG. 19, illustrating the transthoracic delivery of two devices embodying features of the invention to treat a ventricular aneurysm and an enlarged ventricle simultaneously.

FIG. 21 illustrates a similar situation in which membranes 529, 531 are introduced thoracoscopically to threat a ventricular aneurysm 532 and an enlarged ventricle 533. In this embodiment, both of the membranes are introduced through a single thoracoscope 537, with membrane 529 being implanted first, followed by membrane 531.

If desired, the partitioning devices can be constructed to facilitate removal from the hollow organ after a period of time. In the case of morbid obesity, for example, the devices can be implanted in the stomach, and in the event that they becomes too uncomfortable, they can be removed in the same manner in which they were installed.

The invention has a number of important features and advantages. It permits diseases caused by dysfunction of hollow organs to be treated simply and effectively without difficult surgical procedures.

While particular forms of the invention have been illustrated and described herein, it will be apparent that various modifications and improvements can be made to the invention. For example an inflatable dividing element may be used to occlude an atrial appendage of the heart. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is intended that this invention to be defined by the scope of the appended claims as broadly as the prior art will permit.

Terms such a "element", "member", "device", "section", "portion", "steps", "means" and words of similar import when used herein shall not be construed as invoking the provisions of 35 U.S.C. §112(6) unless the following claims expressly use the terms "means" followed by a particular function without specific structure or "step" followed by a particular function without specific action. All patents and patent applications referred to above are hereby incorporated by reference in their entirety. Accordingly, it is not intended that the invention be limited, except as by the appended claims.

What is claimed:

1. A device for improving a patient's cardiac function by partitioning a chamber of the patient's heart, comprising:
a frame construction that has a leading distal portion, that has a plurality of frame elements each of which is secured by an end thereof to the leading distal portion of the frame construction and the frame elements having a plurality of proximal ends configured to expand outwardly to engage the interior of the heart chamber and that is movable from a collapsed state, wherein the frame construction has a small cross-dimension to allow the frame construction to be advanced through a passageway of a delivery catheter into a chamber of the patient's heart, and expanded within the heart chamber to an expanded state wherein the frame construction, after leaving the passageway of the delivery catheter and having been located in an installed position in the heart chamber, has a cross-dimension substantially larger than the small diameter of the tubular passage;
at least two anchor formations which are configured to be advanced through the passageway of the delivery catheter to the chamber of the heart with the frame construction, having at least one anchoring portion that is positioned and capable of anchoring to tissue of the patient's heart wall which defines at least in part the patient's heart chamber to anchor the device in the installed position solely to the tissue of the heart wall within the chamber and without any anchoring structure outside of the chamber, the anchoring portions being spaced from one another to allow for positioning of the device at a select angle relative to the heart chamber, and a membrane which is secured to a proximal side of the frame construction and which is in a folded condition while being fed through the delivery catheter, and which is in an unfolded condition after leaving the delivery catheter so as to define a pressure receiving surface which partitions the heart chamber into functional and non-functional portions.

2. The device of claim 1, comprising a third anchor formation, anchor portions of the anchor formations being positioned at corners of a triangle to allow for positioning of the frame construction with the membrane in a select plane relative to the heart chamber.

3. The device of claim 1, wherein the anchoring portions have sharp ends that penetrate into tissue of the heart wall.

4. The device of claim 3, wherein at least some of the anchoring formations are anchoring hooks.

5. The device of claim 4, wherein at least some of the anchoring hooks are distal anchoring hooks on a distal portion of the frame construction and rotate into the tissue of the heart wall while a catheter forming the tubular passage is withdrawn off the frame construction.

6. The device of claim 5, wherein partial withdrawal of the catheter off a distal portion of the frame construction causes expansion of the distal portion of the frame construction and movement of the distal anchoring hooks away from a center line of the tubular passage, so that the sharp ends of the distal anchoring hooks move into contact with the tissue of the heart wall, and further withdrawal of the catheter off the frame construction causes rotation of the distal anchoring hooks into the tissue of the heart wall.

7. The device of claim 6, wherein a proximal portion of the frame construction expands after leaving the tubular passage, expansion of the proximal portion of the frame construction causing rotation of the distal anchoring hooks into the myocardium.

8. The device of claim 4, wherein at least some of the anchoring hooks are proximal anchoring hooks on a proximal portion of the frame construction, the proximal portion of the frame construction expanding after leaving the tubular passage, expansion of the proximal portion of the frame construction causing movement of the proximal anchoring hooks away from a center line of the tubular passage so that the proximal anchoring hooks move into contact with the tissue of the heart wall.

9. The device of claim 1, wherein the frame construction includes a main frame surrounding a vertical axis and comprising a sequence of sections that alternate in upward and downward directions, expansion of the frame construction moving the sections apart.

10. The device of claim 9, wherein, when viewed from above, the frame construction is deformable into various non-circular shapes to allow for positioning thereof in endocardial cavities having differing non-circular shapes.

11. The device of claim 1, wherein, when viewed from above, the frame construction surrounds a vertical axis and is deformable into various non-circular shapes to allow for positioning thereof in endocardial cavities having differing non-circular shapes.

12. The device of claim 1, wherein the frame construction includes a main frame that expands away from a center line of the tubular passage, and a support frame which, when the main frame is in the expanded state, is mounted to the main frame within an opening defined by the main frame, the support frame supporting the membrane.

13. The device of claim 12, wherein the support frame, when the main frame is in the collapsed state, is collapsed into an elongated arrangement extending along a length of the tubular passage.

14. The device of claim 13, wherein the support frame has at least two elements that pivot relative to one another in a scissor-like manner.

15. The device of claim 1, wherein the membrane is within the frame construction when the frame construction is in the collapsed state.

16. The device of claim 1, wherein the membrane is at least 5 cm in diameter.

17. The device of claim 1 wherein the heart chamber that is partitioned is a left ventricle.

18. The device of claim 1 further comprising a stem extending distally from the membrane.

19. The device of claim 1 wherein the anchoring portions are positioned and capable of anchoring the device so that the membrane is in a non-parallel position relative to the heart chamber wall.

20. A device for improving a patient's cardiac function by partitioning a ventricle of the patient's heart, comprising:

a frame construction that has a leading distal portion, that has a plurality of frame elements each of which is secured by an end thereof to the leading distal portion of the frame construction and the frame elements having a plurality of proximal ends configured to expand outwardly engage the interior of the ventricle and that is movable from a collapsed state, wherein the frame construction has a small cross-dimension to allow the frame construction to be advanced through a passageway of a delivery catheter into the ventricle, and expanded within the ventricle to an expanded state wherein the frame construction, after leaving the passageway of the delivery catheter and having been located in an installed position in the ventricle, has a cross-dimension substantially larger than the small diameter of the tubular passage;

at least two anchor formations having at least one anchoring portion that is positioned and capable of anchoring solely to tissue of the wall of the ventricle within the ventricle and without any anchoring structure outside of the ventricle to anchor the device in the installed position to the tissue of the wall of the ventricle, the anchoring portions being spaced from one another to allow for positioning of the device at a select angle relative to the ventricle, and a membrane which is secured to a proximal side of the frame construction and which is in a folded condition while being fed through the delivery catheter, and which is in an unfolded condition after leaving the delivery catheter so as to define a pressure receiving surface which partitions the ventricle into functional and non-functional portions; and, wherein the frame construction is configured to support the membrane wherein a ventricular pressure of at least 60 mm Hg acts on the pressure receiving surface.

21. A partitioning device for improving cardiac function, comprising:

a reinforced membrane that is movable from a folded condition, wherein the reinforced membrane can be fed through a tubular passage having a small cross-sectional area to a chamber of a heart of a patient, to an unfolded condition after leaving the tubular passage, in the unfolded condition the reinforced membrane having an area configured to partition the a chamber of the heart into functional and non-functional portions; and at least one anchor formation connected to the reinforced membrane, wherein the at least one anchor formation can be fed with the membrane through a tubular passage having a small cross-sectional area to the chamber of the heart, the anchor formation having at least one anchoring portion that is positioned and capable of anchoring to tissue of the heart wall after leaving the tubular passage, and so anchor the reinforced membrane in the installed position solely to the tissue of the heart wall within the heart chamber and without any anchoring structure outside of the heart chamber.

22. The partitioning device of claim 21, wherein the reinforced membrane includes a frame construction with a main frame surrounding a vertical axis and comprising a sequence of sections that alternate in upward and downward directions, expansion of the frame construction moving the sections apart.

23. The device of claim 21 wherein the chamber of the heart that is partitioned is a left ventricle.

24. The device of claim 21 further comprising a stem extending distally from the membrane.

25. The device of claim 21 wherein the anchoring portions are positioned and capable of anchoring the device so that the membrane is in a non-parallel position relative to the heart chamber wall.

26. A partitioning device for improving cardiac function, comprising:

a reinforced membrane that is movable from a folded condition, wherein the reinforced membrane can be fed through a tubular passage having a small cross-sectional area, to an unfolded condition after leaving the tubular passage, in the unfolded condition the reinforced membrane having an area configured to partition a ventricle of a heart of a patient into functional and non-functional portions;

at least one anchor formation connected to the reinforced membrane, the anchor formation having at least one anchoring portion that is positioned and capable of anchoring to tissue of a wall of the ventricle, and so anchor the reinforced membrane in the installed position solely to the tissue of the wall within the ventricle and without any anchoring structure outside of the ventricle; and, wherein the reinforced membrane is sufficiently strong to withstand a ventricular pressure of at least 60 mm Hg.

27. The partitioning device of claim 26 wherein the support frame, when the main frame is in the collapsed state, is collapsed into an elongated arrangement extending along a length of the tubular passage.

28. The partitioning device of claim 27, wherein the support frame has at least two elements that pivot relative to one another in a scissor-like manner.

29. A device for treating a patient with congestive heart failure by partitioning a chamber of the patient's heart into a main functional portion and a secondary non-functional portion, comprising:

(a) a reinforced, partitioning component having a folded configuration for delivery through a delivery catheter to a chamber of the patient's heart and an expanded configuration for deployment within the heart chamber so as to partition the heart chamber into a main functional portion and a secondary non-functional portion, wherein the reinforced partitioning component has a distally extending stem; and (b) securing members on a periphery of the reinforced partitioning component which are configured for delivery through the delivery catheter to the chamber of the patient's heart to secure the periphery of the reinforced partitioning component in the expanded configuration to a wall defining at least in part the patient's heart chamber to thereby partition the chamber into a main functional portion and a secondary non-functional portion.

30. The device of claim 29 wherein the partitioning component has a pressure receiving surface.

31. The device of claim 30 wherein the pressure receiving surface is a concave surface.

32. The device of claim 30 wherein the pressure receiving surface of the partitioning component is at least in part a membrane.

33. The device of claim 32 wherein the membrane is reinforced by a radially expandable frame.

34. The device of claim 32 wherein the radially expandable frame has a plurality of ribs.

35. The device of claim 33 wherein the ribs have free proximal ends and secured distal ends and the secured distal ends are configured to facilitate abduction of the free proximal ends away from a centerline axis to facilitate expansion of the reinforced membrane.

36. The device of claim 35 wherein the distal ends of the ribs are pivotally secured.

37. The device of claim 35 wherein the securing elements configured to secure the periphery of the partitioning component are disposed on free proximal ends of the ribs.

38. The device of claim 37 wherein the securing elements have tissue penetrating tips.

39. The device of claim 32 wherein the membrane is secured to the ribs on a proximal side of the expandable frame.

40. The device of claim 32 wherein the membrane is formed at least in part of a biocompatible material.

41. The device of claim 40 wherein the biocompatible material is selected from the group consisting of expanded fluoropolymer, polyethylene terephthalate and polypropylene.

42. The device of claim 40 wherein the biocompatible material is in the form of a mesh.

43. The device of claim 29 wherein the partitioning component is configured to have a lenticular shape when in the expanded configuration.

44. The device of claim 29 wherein the stem of the reinforced partitioning component is configured to be secured to a heart wall defining at least in part the secondary portion of the patient's heart chamber.

45. The device of claim 44 wherein the stem has a free helically shaped tip for securing the stem to a region of a heart wall defining in part the heart chamber to be partitioned.

46. The device of claim 45 wherein the pressure receiving surface has at least in part a conical shape.

47. The device of claim 29 wherein the patient's heart chamber that is partitioned is a left ventricle.

* * * * *